(12) United States Patent
Hallen

(10) Patent No.: US 11,147,636 B2
(45) Date of Patent: Oct. 19, 2021

(54) SURGICAL SUITE INTEGRATION AND OPTIMIZATION

(71) Applicant: Novartis AG, Basel (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 431 days.

(21) Appl. No.: 16/149,415

(22) Filed: Oct. 2, 2018

(65) Prior Publication Data

US 2019/0099226 A1 Apr. 4, 2019

Related U.S. Application Data

(60) Provisional application No. 62/567,875, filed on Oct. 4, 2017.

(51) Int. Cl.
| | |
|---|---|
| *A61B 3/113* | (2006.01) |
| *A61B 3/10* | (2006.01) |
| *A61B 18/20* | (2006.01) |
| *A61B 3/14* | (2006.01) |
| *A61F 9/008* | (2006.01) |
| *A61B 34/00* | (2016.01) |
| *A61B 34/10* | (2016.01) |
| *A61B 3/00* | (2006.01) |

(Continued)

(52) U.S. Cl.
CPC ............ *A61B 34/25* (2016.02); *A61B 3/0025* (2013.01); *A61B 34/10* (2016.02); *A61B 90/361* (2016.02); *A61B 90/37* (2016.02); *A61F 9/008* (2013.01); *A61F 9/00821* (2013.01); *A61F 9/00825* (2013.01); *H04N 13/324* (2018.05); *H04N 13/332* (2018.05); *H04N 13/398* (2018.05); *A61B 90/98* (2016.02); *A61B 2017/00203* (2013.01); *A61B 2017/00216* (2013.01); *A61B 2034/105* (2016.02); *A61B 2034/2048* (2016.02); *A61B 2034/2065* (2016.02); *A61B 2034/252* (2016.02); *A61B 2034/254* (2016.02); *A61B 2090/372* (2016.02); *A61B 2090/378* (2016.02); *A61B 2090/3735* (2016.02); *A61F 2009/00846* (2013.01); *A61F 2009/00851* (2013.01); *A61F 2009/00897* (2013.01); *H04N 7/15* (2013.01); *H04N 2213/008* (2013.01)

(58) Field of Classification Search
CPC ... A61B 2090/3735; A61B 3/13; A61B 34/25; A61B 34/10; A61B 3/145; A61B 3/14; A61B 90/30; A61B 90/37; A61F 2009/00846; A61F 2009/00851; A61F 2009/00863; A61F 9/00736
See application file for complete search history.

(56) References Cited

U.S. PATENT DOCUMENTS

| | | | | |
|---|---|---|---|---|
| 2009/0275929 | A1* | 11/2009 | Zickler | A61F 9/00804 606/5 |
| 2014/0005555 | A1* | 1/2014 | Tesar | A61B 17/0293 600/476 |
| 2015/0173846 | A1* | 6/2015 | Schneider | A61B 5/748 600/424 |

* cited by examiner

*Primary Examiner* — Jon Eric C Morales

(57) ABSTRACT

Systems, methods, and computer-readable media for integrating and optimizing a surgical suite. An ophthalmic suite can include a surgical console, a heads-up display communicatively coupled with a surgical camera for capturing a three-dimensional image of an eye, and a surgical suite optimization engine. The surgical suite optimization engine can performs a wide variety of actions in response to action codes received from the other components in the surgical suite. The surgical suite optimization engine can be integrated within another component of the surgical suite, can be a stand-alone module, and can be a cloud-based tool.

37 Claims, 23 Drawing Sheets

(51) Int. Cl.
*H04N 13/332* (2018.01)
*H04N 13/398* (2018.01)
*H04N 13/324* (2018.01)
*A61B 90/00* (2016.01)
*H04N 7/15* (2006.01)
*A61B 17/00* (2006.01)
*A61B 90/98* (2016.01)
*A61B 34/20* (2016.01)

SURGICAL SUITE INTEGRATION AND OPTIMIZATION

BACKGROUND

Field of the Disclosure

The present disclosure relates to ophthalmic surgery, and more specifically, to systems, methods, and computer-readable media for integrating and optimizing a surgical suite.

Description of Related Art

Surgical consoles, imaging devices, laser devices, diagnostic devices, and other accessories that are used in ophthalmic surgery can generate, record, and transmit data relating to features of a surgery, procedure steps and stages, etc. However, the separate devices that make up a surgical suite are currently not adequately connected.

Furthermore, ophthalmic surgery is commonly performed using an operating microscope to visualize various structures in the eye. However, many ophthalmic surgeries take a considerable amount of time. For example, vitreoretinal surgery can last over three hours in length. Over the course of these long surgeries, surgeons can become fatigued after being bent over a microscope eyepiece. A high dynamic range digital camera system can be used to capture a multidimensional visualization of a patient's eye that can be transmitted to a high-definition display. While such displays allow a surgeon to conduct surgery in a heads-up posture, the potential for using stereoscopic visualization on a heads-up display capable of performing advanced operations for improving other areas of a surgical practice is not currently realized.

SUMMARY

The disclosed embodiments of the present technology relate to systems, methods, and computer-readable media are disclosed for integrating and optimizing a surgical suite. Some embodiments involve an ophthalmic system that includes a surgical console and a heads-up display communicatively coupled with a surgical camera for capturing a three-dimensional image of an eye. The heads-up display can display a stereoscopic representation of the three-dimensional image of the eye and a viewer can wear three-dimensional glasses to view the three-dimensional image of the eye.

The surgical console can have tools for conducting an ophthalmic procedure and can monitor quantitative features of the ophthalmic procedure. The surgical console can determine to transmit an action code relating to the quantitative feature of the ophthalmic procedure in a variety of circumstances.

The ophthalmic system also includes a surgical suite optimization engine that performs a wide variety of actions in response to action codes received from the surgical console or other components of a surgical suite. In some cases, the surgical suite optimization engine can be integrated in the heads-up display, integrated within another component of the surgical suite, a stand-alone module, a cloud-based tool, etc.

The surgical console can monitor and/or transmit, to the surgical suite optimization engine, procedure data describing a plurality of procedure steps for a plurality of ophthalmic procedures. In some cases, the surgical console monitors a control limit for an aspect of one or more procedure step and can issue an action code when the aspect of the one or more procedure step comes within a predetermined proximity to the control limit. In these cases, the surgical suite optimization engine can perform an action of displaying an alert relating to the proximity to the control limit.

In some cases, the procedure data can also describe a plurality of surgical phases and/or procedure steps. In some cases, the surgical console issues an action code at a transition between surgical steps and/or phases. The surgical suite optimization engine can perform a variety of actions when it receives the action code indicating a transition between steps and/or stages including, but not limited to: automatically adjusting display parameters of the stereoscopic representation of the three-dimensional image of the eye; displaying one or more overlay over the stereoscopic representation of the three-dimensional image of the eye; filtering color attributes of the stereoscopic representation of the three-dimensional image to highlight one or more areas of the eye in the stereoscopic representation of the three-dimensional image; enhancing image features of the stereoscopic representation of the three-dimensional image; moving, with a robotic arm, the heads-up display relative to the position of the surgeon at the transition between surgical phases to optimize a stereoscopic viewing distance of the first region of the eye to a position to optimize a stereoscopic viewing distance of the second region of the eye; causing a diagnostic imaging device to focus on an area of the eye.

The ophthalmic system can also include a laser treatment component and the surgical suite optimization engine can perform, at a transition point between laser treatment steps, digital signal processing to maximize red contract of the stereoscopic representation of the three-dimensional image of the eye when the laser treatment transitions from the emission of the treatment beam to the emission of the aiming beam and to neutralize a green flashback from a retina in the stereoscopic representation of the three-dimensional image of the eye when the laser treatment transitions from the emission of the aiming beam to the emission of the treatment beam.

In some cases, the procedure data can also describe user preference data describing a surgeon's or other surgical staff member's preference for one or more procedure step for an ophthalmic procedure.

In some cases, the surgical console can monitor an operational status of a component of the surgical console and can issue an action code when the component malfunctions. The surgical suite optimization engine can receive the action code describing the malfunction and automatically establish a video conference connection with a technical support center.

In some cases, the heads-up display can display a dashboard that includes a main surgical view window displays the stereoscopic representation of a three-dimensional image of an eye along with a variety of menus, icons, picture-in-picture displays, graphical overlays on top of the image of the eye, etc. The stereoscopic representation of the three-dimensional image of the eye can also be digitally adjusted to focus on certain anatomy, to sharpen certain regions, to change color of the image, etc.

In some cases, the dashboard can be controlled by a touchpad interface, a touchscreen interface, a voice control interface, etc. In some cases, the three-dimensional glasses can contain a motion tracker tracks movement of the wearer's gaze and can transmit a gaze signal to the surgical suite optimization engine. The surgical suite optimization engine can use the gaze signal to display and move a pointer on the display and activate functions of the dashboard tools, menus, etc.

The surgical suite optimization engine integrates and synergistically optimizes a wide variety of surgical functions. The surgical suite optimization engine can also include a transcode engine for interpreting communications from a surgical suite, machine learning and artificial intelligence modules for learning how to optimize procedure to maximize patient outcome, speech recognition modules to learn and disambiguate voice inputs into known voice commands.

BRIEF DESCRIPTION OF THE DRAWINGS

For a more complete understanding of the present technology, its features, and its advantages, reference is made to the following description, taken in conjunction with the accompanying drawings, in which.

DESCRIPTION

Systems, methods, and computer-readable media are disclosed for integrating and optimizing a surgical suite. In some embodiments of the disclosed technology, surgical consoles, imaging devices, laser devices, diagnostic devices, and other accessories that are used in ophthalmic surgery are integrated in an inter-networked surgical suite. The inter-networked surgical suite can include a surgical camera that generates high-definition images of eye anatomy and transmits the images to a heads-up display for three-dimensional stereoscopic visualization of the anatomy. Some embodiments of the disclosed technology involve a surgical suite optimization engine for performing advanced operations for improving surgical practice and patient outcome.

Figure 1:
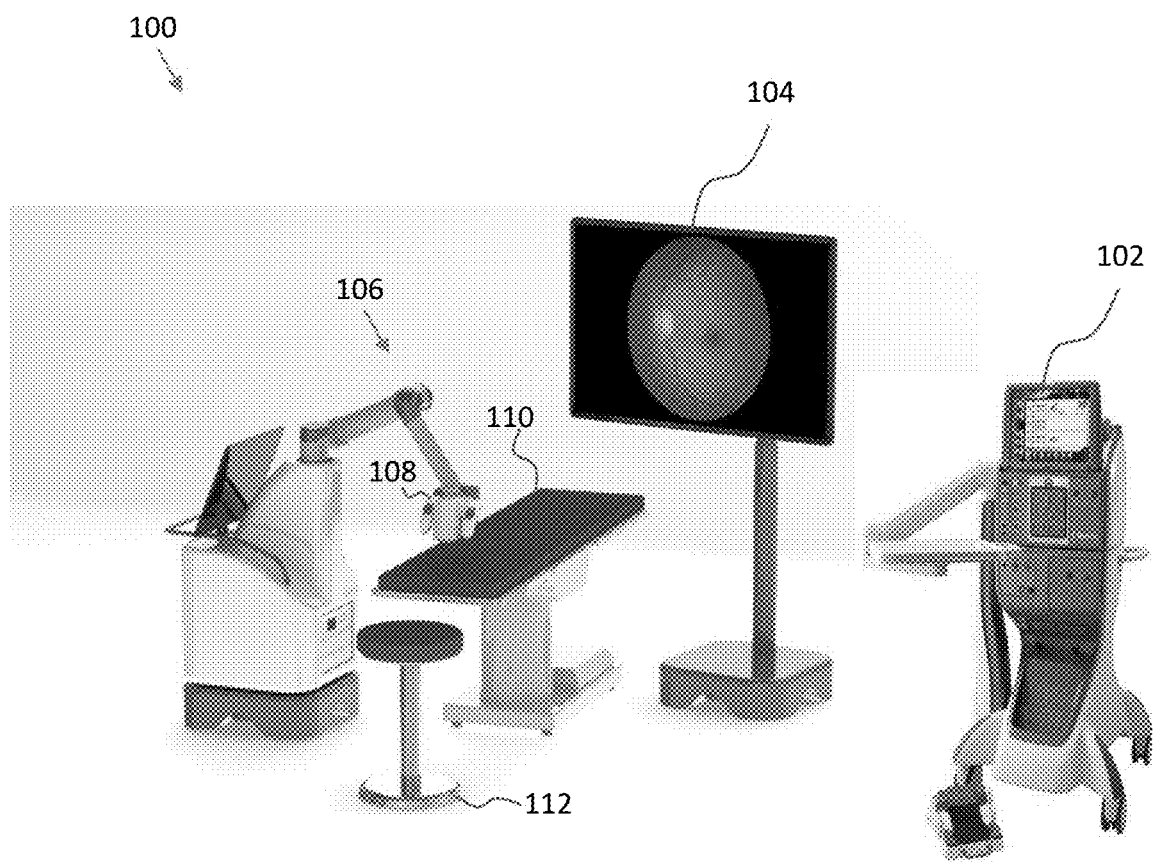
FIG. 1 illustrates an ophthalmic suite including a surgical console, a heads-up display, and a surgical camera system.

FIG. 1 illustrates an ophthalmic suite 100 including a surgical console 102, a heads-up display 104, and a surgical camera system 106 that positions a surgical camera 108 over a patient table 110. The surgical camera 108 can be a High Dynamic Range (HDR) camera with a resolution, image depth, clarity and color contrast that enables a high quality, three-dimensional image of patient anatomy. For example, the present disclosure describes an HDR camera used to resolve high quality, three-dimensional views of an eye as well as surgical consoles and heads-up displays for performing actions during ophthalmic procedures that use the HDR camera. However, those with ordinary skill in the art having the benefit of the present disclosure will readily appreciate that the disclosed technology can be applied to various other fields of anatomical diagnostics, surgery, etc.

The surgical camera 108 can be communicatively coupled with the heads-up display 104 (e.g. via a wired connection, a wireless connection, etc.) and the heads-up display 104 can display a stereoscopic representation of the three-dimensional image providing a surgeon, staff, students, and other observers depth perception into the eye anatomy. The surgical camera 108 can also be used to increase magnification of the eye anatomy while maintaining a wide field of view. The stereoscopic representation of the three-dimensional image can be viewed on the heads-up display with stereoscopic glasses, as an autostereogram, using Fresnel lenses, etc. With the stereoscopic representation of the three-dimensional image displayed on the heads-up display 104, a surgeon can perform procedures on a patient's eye while in a comfortable position (e.g. sitting on a stool 112) without bending over a microscope eyepiece and straining his neck.

The surgical console 102 can be communicatively coupled with the heads-up display 104 and/or the surgical camera system 106. In some embodiments, the heads-up display 104 can receive information (e.g. surgical parameters) from the surgical console 102 and display the information on the heads-up display 104 along with the stereoscopic representation of the three-dimensional image. The surgical console 102 can also send signals to the heads-up display 104 for performing operations (e.g. starting and stopping video recording).

In addition, ophthalmic suite 100 can also include a surgical suite optimization engine (not shown) containing one or more processors (not shown) and memory (not shown) for performing advanced operations. As explained in greater detail below, the surgical suite optimization engine can integrate a surgical suite and can perform a wide variety of actions to synergistically optimize a wide variety of surgical functions. For example, the surgical suite optimization engine can: enable gaze-tracking to navigate a display dashboard; perform digital signal processing for adjusting display settings, applying filters, increasing contrast, neutralizing particular wavelengths, identifying anatomy, etc.; display of a wide variety of images at various zoom depths, menus, other diagnostic images, surgical productivity applications, surgical schedules, live video teleconferencing, etc.; control robotic arms to move the heads-up display to optimize stereopsis or ensure centration of the surgical camera; control a diagnostic device to automatically focus on anatomy based on the procedural step; provide alerts and recommendations to surgical staff; modulate color effects during laser treatment; etc.

Also, surgical suite optimization engine can include a network interface that allows the surgical suite optimization engine to communicate with the surgical camera system 106, the surgical console 102, and other surgical systems. In some cases, the surgical suite optimization engine can serve to inter-network some or all of network-capable components in a surgical suite 100.

Inter-networking the surgical suite can allow for advancements in surgical practice and patient outcome. For example, the surgical console 102 can include a wide assortment of tools for performing various aspects of ophthalmic procedures and can include memory (not shown) and one or more processors (not shown) for controlling the tools as well as monitoring a wide variety of quantitative features of a surgical procedure. When the surgical console 102 is connected with the surgical suite optimization engine, the surgical console 102 send information about the quantitative features of a surgical procedure (e.g. via one or more action codes) to the surgical suite optimization engine. In response, the surgical suite optimization engine can interpret the information from the surgical console 102 perform actions that improve other areas of a surgical procedure or a surgical practice. More generally, the surgical suite optimization engine can receive, via the network interface, an assortment of information from any of components in the surgical suite 100 and, in response to the gathered information, perform actions that improve a wide variety of areas of a surgical procedure or a surgical practice, resulting in better patient outcomes.

Figure 2A:
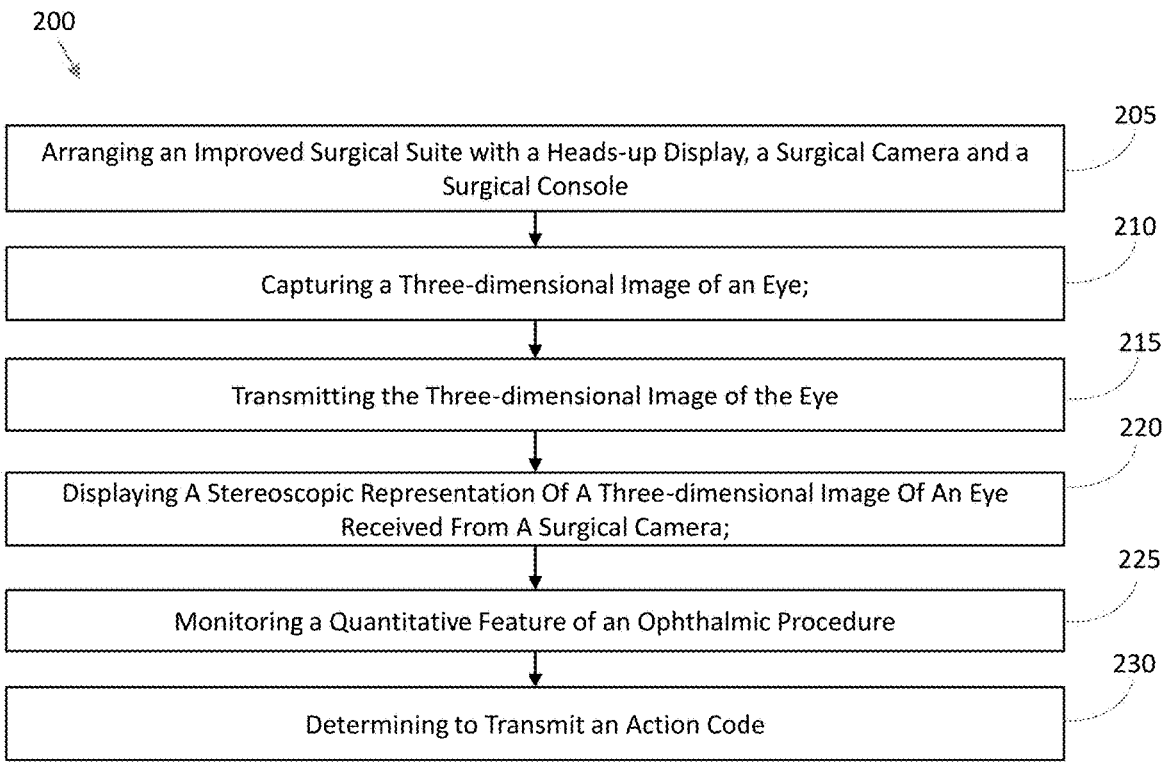
FIGS. 2A and 2B illustrate methods of improving a surgical procedure using surgical suite optimization engine.

FIG. 2A illustrates a method 200 of improving a surgical procedure using a surgical suite optimization engine. The method 200 involves arranging an improved surgical suite with a heads-up display containing a surgical suite optimization engine, a surgical camera, and a surgical console 205. In some cases, the heads-up display, the surgical camera, and the surgical console are communicatively coupled via a wireless connection.

The method 200 further involves the surgical camera capturing a three-dimensional image of an eye 210 and transmitting the three-dimensional image of the eye to the heads-up display 215. Next, the method 200 involves displaying a stereoscopic representation of the three-dimensional image of the eye on the heads-up display 220.

Also, the method 200 involves monitoring a quantitative feature of an ophthalmic procedure 225 and the surgical console determining to transmit an action code to the surgical suite optimization engine of the heads-up display 230.

Figure 2B:
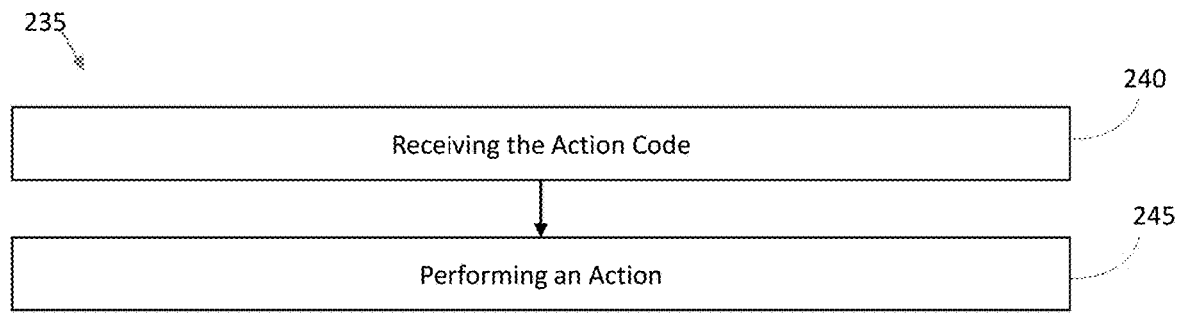

FIG. 2B illustrates another method 235 of improving a surgical procedure using surgical suite optimization engine. The method 235 can also involve the surgical suite optimization engine receiving the action code 240 and performing an action 245 in response to the action code. As explained above, a surgical console can monitor a wide variety of quantitative features of ophthalmic procedures and can process a variety of instructions for determining when to transmit an action code. Likewise, the surgical suite optimization engine can perform a wide variety of actions in response to receiving the action codes. Specific examples of monitoring a procedure, determinations by the surgical console to issue action codes, and specific actions by the surgical suite optimization engine are described in greater detail below. However, those with ordinary skill in the art having the benefit of the present disclosure will readily appreciate that a wide variety of other aspects of a surgical practice can benefit from the disclosed technology.

Figure 3A:
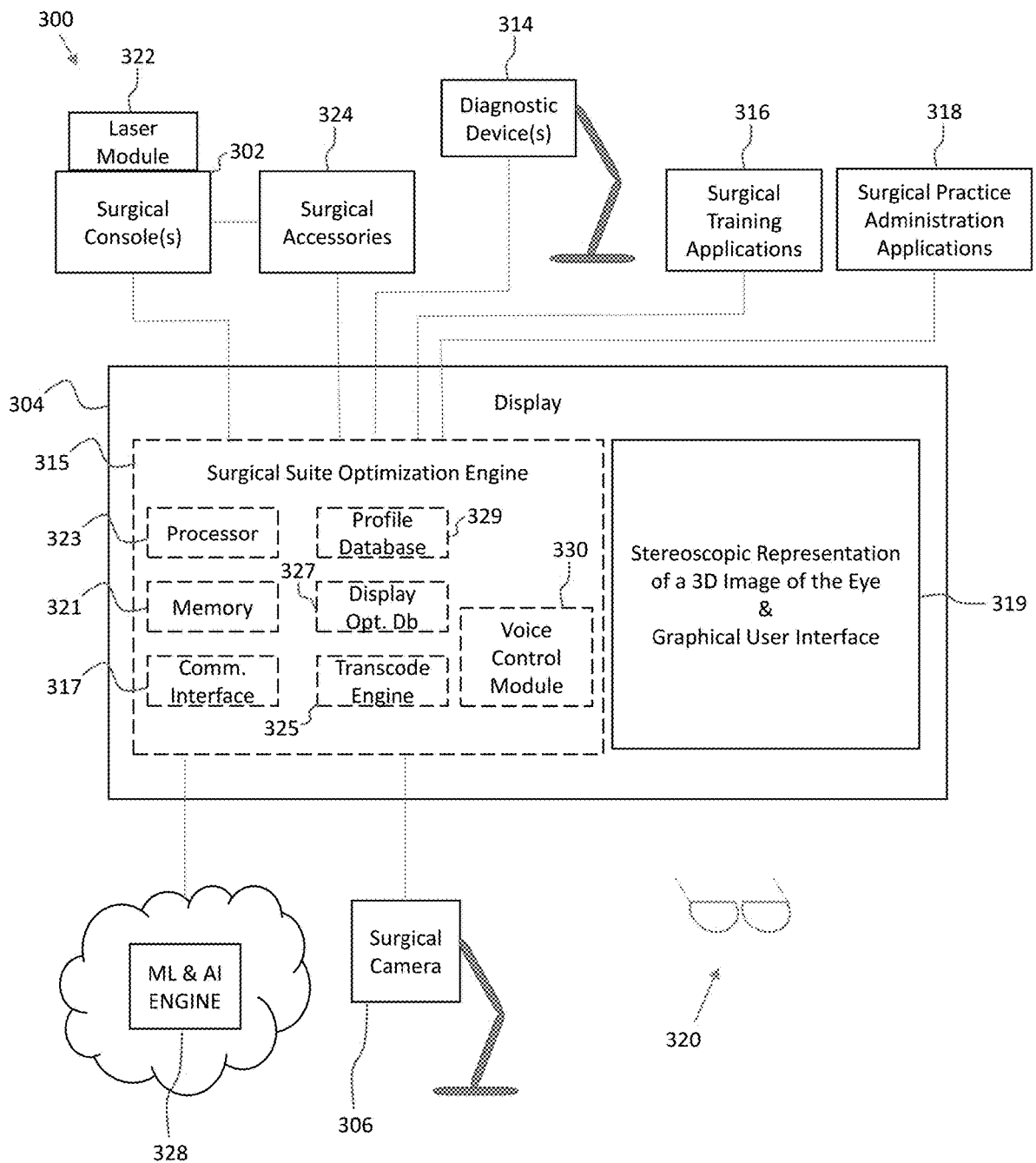
FIGS. 3A-3C illustrate a surgical suite optimization engine running on a heads-up display in an ophthalmic surgery suite

FIG. 3A illustrates a surgical suite optimization engine 315 running on a heads-up display 304 in an ophthalmic surgery suite 300. The ophthalmic surgery suite 300 can also include a surgical camera 306 and one or more surgical console(s) 302. The surgical camera 306 and the surgical console(s) 302 are communicatively coupled with the surgical suite optimization engine 315. The surgical suite optimization engine 315 includes a processor 323 and memory 321 that contains instructions for performing a variety of actions. In some cases, the surgical suite optimization engine includes an additional graphical processing unit (not shown) for performing digital image post-processing and other advanced graphical operations. The surgical suite optimization engine 315 can also contain a communication interface 317 that can wirelessly communicate with the surgical camera 306, the surgical console(s) 302, and other devices. In some cases, the surgical suite optimization engine 315 is communicatively coupled with a cloud-based Machine Learning and Artificial Intelligence engine 328.

The surgical camera 306 can capture an image of a patient's eye. In some cases, the surgical camera 306 is a HDR that captures a three-dimensional image of the patient's eye. The surgical camera 306 can transmit the three-dimensional image of the patient's eye to the heads-up display 304 and the heads-up display 304 can display a stereoscopic representation of the three-dimensional image of the eye in a Graphical User Interface 319. The stereoscopic representation of the three-dimensional image of the eye can be viewed by a surgeon, surgical staff, students, etc. using 3D glasses 320. In some cases, the heads up display can comprise a high definition wide-screen display, a computer display, a tablet, a smartphone, etc. The heads-up display 304 can also include touchscreen capability, voice control capability, gaze-enabled control (as described below), etc.

The surgical console(s) 302 can include tools for conducting a variety of ophthalmic procedures. For example, the surgical console(s) 302 can include tools for performing cataract surgery, inter-ocular (IOL) lens placement, vitreo-retinal surgery, glaucoma surgery, laser refractive surgery, etc. Although specific examples of ophthalmic surgeries are listed herein, those with ordinary skill in the art having the benefit of the present disclosure will readily recognize that a wide variety of surgery types (ophthalmic or otherwise) can benefit from the present technology. The surgical console(s) 302 can also include a processor (not shown) and memory (not shown) containing instructions that, when executed by the processor, cause the surgical console(s) 302 to operate the tools, monitor features of the surgery, guide a surgical staff through steps and stages of a surgical procedure, etc. Further, as explained in more detail below, the processor, cause the surgical console(s) 302 to determine when to transmit an action code relating to a feature of an ophthalmic procedure to the surgical suite optimization engine 315.

The surgical console(s) 302 can also be coupled with a laser module 322 and a variety of surgical accessories 324 (e.g. wireless footswitches, handpieces, probes, preloaded IOL delivery systems, aspirators, illuminators, diagnostic devices, micro-stent delivery systems, etc.) for performing surgical procedures. In some cases, the surgical accessories contain an integrated communication interface (not shown) for communicating with the surgical suite optimization engine 315, either directly or through another component in the surgical suite 300. For example, the surgical suite 300 can include a footswitch (not shown) that can be used to start and stop a video recording feature on the heads-up display 304. Also, as explained in greater detail below, the surgical console(s) 302 can also be coupled with a variety of other devices and applications such as diagnostic devices 314, surgical training applications 316, surgical practice administration applications 318, etc.

In some cases, some or all of the surgical console(s), surgical camera 306, heads-up display 304, laser module 322, surgical accessories 324, diagnostic device(s) 314, surgical training applications 316, surgical practice administration applications 318, and the surgical suite optimization engine 315 are connected as an inter-network of "smart" devices, aka connected as an Internet of Things (IoT). In some cases, the surgical suite optimization engine 315 optimizes the performance of the ophthalmic surgery suite 300 by ingesting data from inter-networked devices and controlling other aspects of the ophthalmic surgery suite 300. In some cases, the surgical suite optimization engine 315 includes a transcode engine 325 for performing a variety of transcoding functions such as one or more of recognizing signals from connected devices, translating the signals, converting signals to a common intermediate language, etc.

In some cases, the surgical suite optimization engine 315 can include a voice control module 330. The voice control module 330 can receive and process voice commands to control an aspect of the surgery (e.g. navigation of a graphical user interface, control of the surgical console, control of settings, etc.) In some cases, the voice control module 330 can recognize a speaker of voice commands and can allow only certain speakers (e.g. surgeon, attending nurse, etc.) to control certain aspects of surgery. Also, in some cases, the voice control module 330 can disambiguate voice inputs (e.g. common parlance) into recognized voice commands. Similarly, the voice control module 330 can communicate with the machine learning and artificial intelligence engine 328 and can learn speech patterns, new vocabulary, etc.

The surgical suite optimization engine 315 can monitor the ophthalmic surgery suite 300, can receive signals (e.g. an action code from the surgical console(s) 302) from connected devices, and can perform a variety of actions to optimize the ophthalmic surgery suite 300. Also, the surgical suite optimization engine 315 can include a display optimization database 327 and a user profile database 329 to further optimize display settings for that particular surgical step, as explained in greater detail below.

As shown in FIG. 3A, the surgical suite optimization engine 315 is integrated in the heads-up display 104. However, the surgical suite optimization engine 315 can be part of a surgical console, a laser console, a diagnostic device, a surgical camera, etc. Also, the surgical suite optimization engine 315 can be a stand-alone device, a cloud-based processing engine, etc.

Figure 3B:
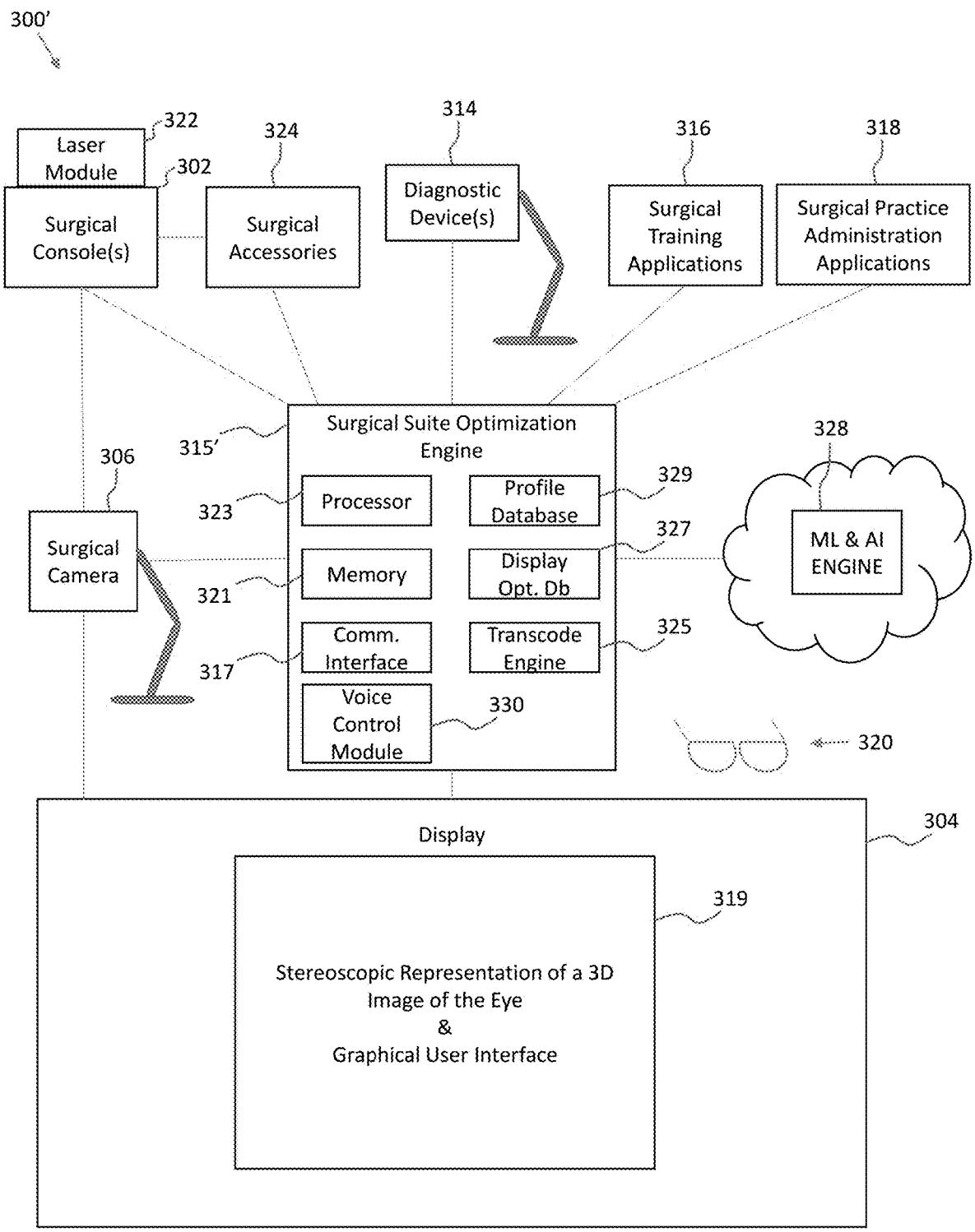

FIG. 3B illustrates a stand-alone surgical suite optimization engine 315' in a surgical suite 300'. The surgical suite optimization engine 315' can be communicatively coupled with the surgical console(s) 302, laser module 322, surgical accessories 324, surgical camera 306, heads-up display 304, cloud-based machine learning and artificial intelligence engine 328, diagnostic device(s) 314, surgical training applications 314, surgical practice applications 318, etc.

Figure 3C:
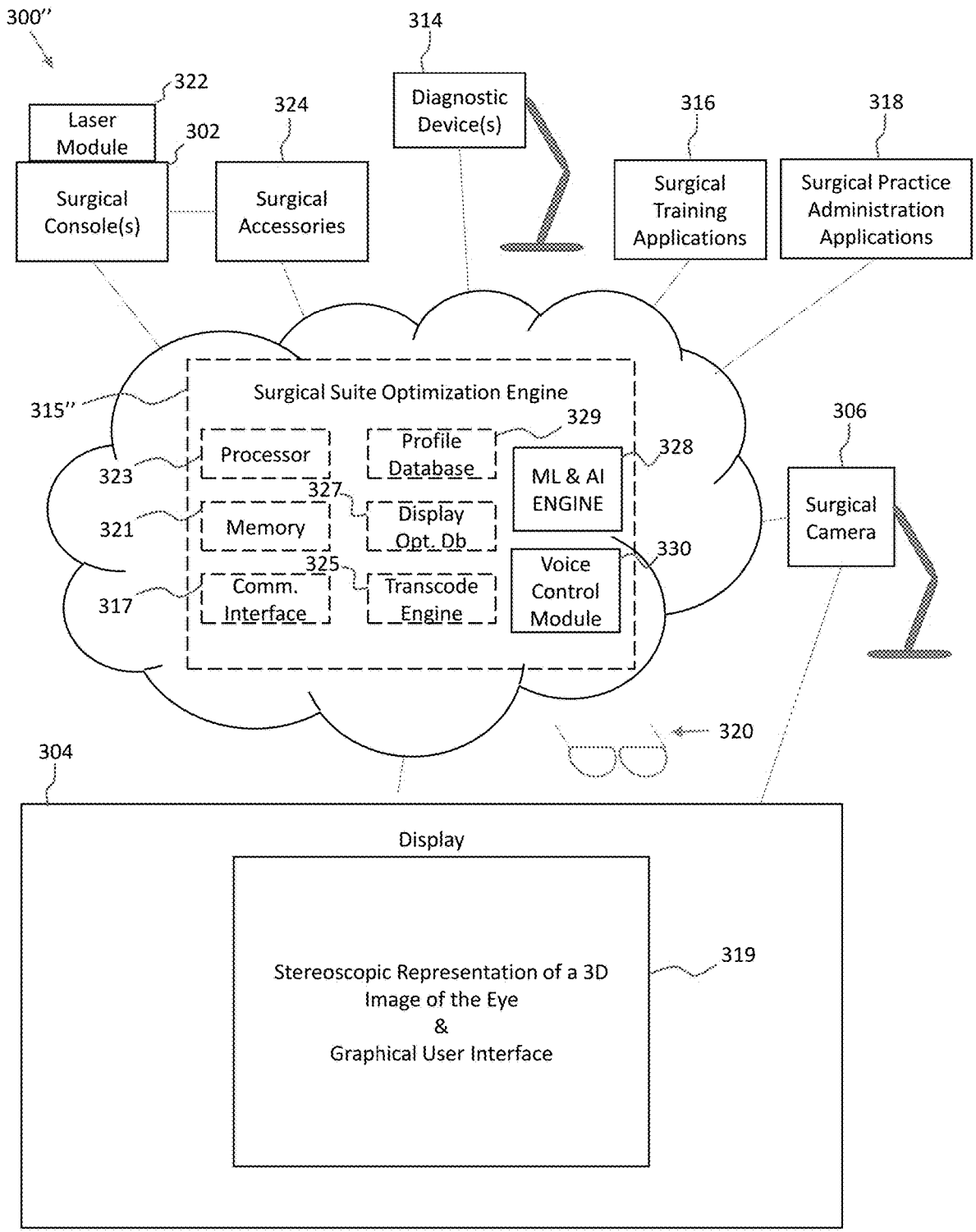

FIG. 3C illustrates a cloud-based surgical suite optimization engine 315" connected with a surgical suite 300". The surgical suite optimization engine 315" can be communicatively coupled with the surgical console(s) 302, laser module 322, surgical accessories 324, surgical camera 306, heads-up display 304, cloud-based machine learning and artificial intelligence engine 328, diagnostic device(s) 314, surgical training applications 314, surgical practice applications 318, etc.

Like the surgical suite optimization engine 315 of FIG. 3A, the stand-alone surgical suite optimization engine 315' and the cloud-based surgical suite optimization engine 315" can monitor the ophthalmic surgery suite 300', 300" and perform actions to optimize the surgical suite and patient outcomes.

Figure 4A:
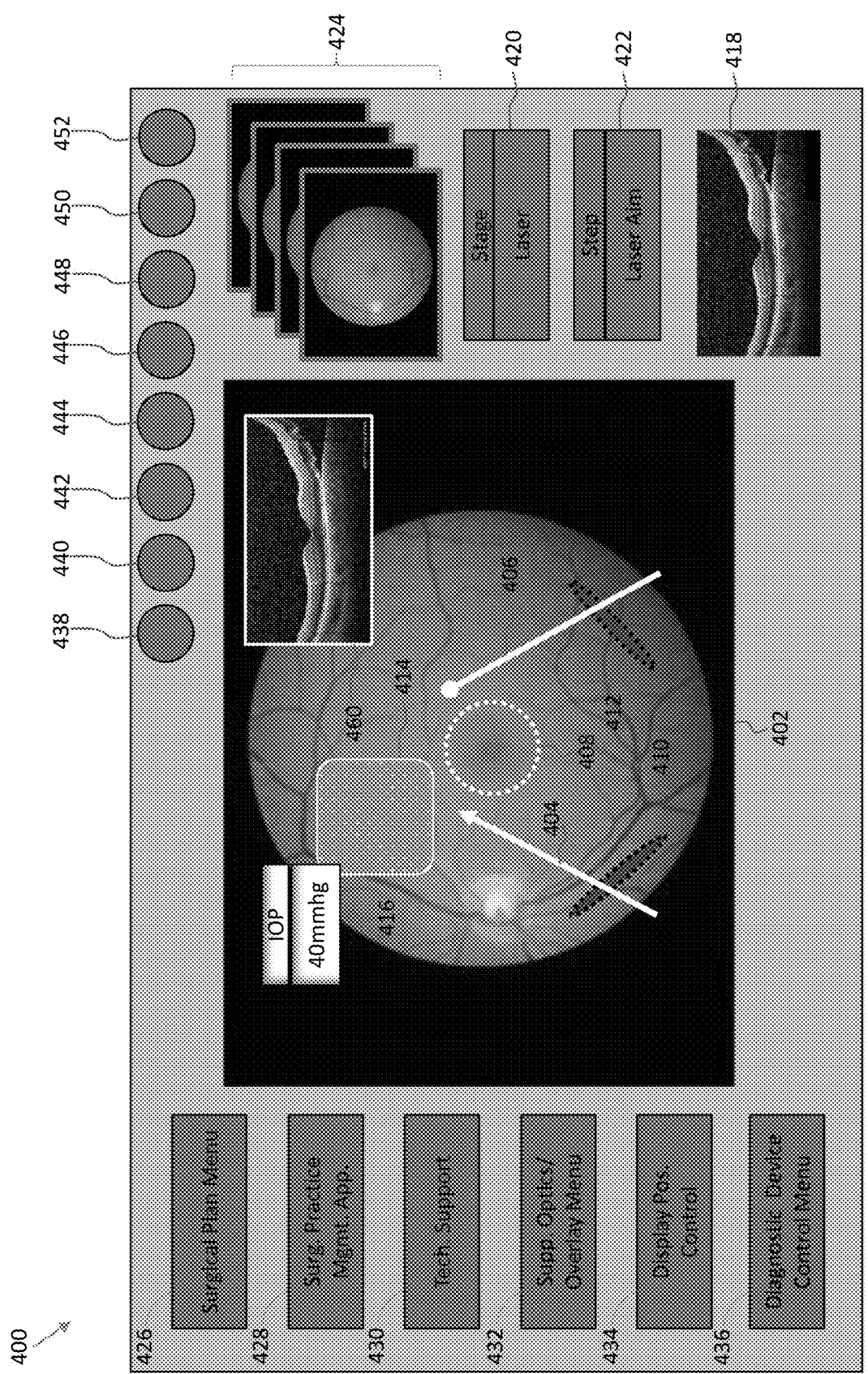
FIG. 4A illustrates representation of a graphical user interface of a display dashboard that can be displayed on a heads-up display in a surgical suite.

FIG. 4A illustrates representation of a graphical user interface (GUI) 400 of a display dashboard that can be displayed on a heads-up display in an ophthalmic suite according to some embodiments of the present technology. The GUI 400 can include a main surgical view window 402 that displays a stereoscopic representation of a three-dimensional image of an eye received from the surgical camera. Also, the image of the eye can show the tools 404, 406 that are being used to perform surgery. In some cases, the stereoscopic representation of the three-dimensional image of the eye can be digitally adjusted to focus on certain anatomy, to sharpen certain regions, to change color of the image, etc. Also, a variety of graphical overlays 408, 410, 412, 414, 416 can be displayed along with the image of the eye. In some cases, the surgical suite optimization module can identify certain anatomy (e.g. the macula) and an anatomical identification overlay 408 can be displayed over the image of the eye. In some cases, a surgical planning application and/or the surgical suite optimization engine can analyze pre-operative images of the eye and provide recommendations for certain aspects of the ophthalmic procedure (e.g. recommended positions for incisions) and the GUI can display incision overlays 410, 412 on the image of the eye to help guide the surgical staff. Also, in some cases where the ophthalmic procedure includes a laser treatment component, the GUI can display a laser targeting overlay 414. Also, the surgical suite optimization engine and/or the heads-up display can receive real-time surgical data (e.g. intraocular pressure) and the GUI can display a real-time surgical data overlay 416.

In addition to the main surgical window 402, the GUI 400 can display a wide variety of additional GUI features that are helpful to a surgical team. For example, the surgical suite can include a diagnostic device (e.g. an Optical Coherence Tomography (OCT) device) and the GUI 400 can display a diagnostic imaging window 418 that include a diagnostic view of eye anatomy. The diagnostic imaging window 418 can display pre-operative diagnostic images, real-time diagnostic images, model images, etc. In some cases, the surgical suite optimization engine can recognize (e.g. based on surgical procedure data, location of surgical tools, etc.) a location of the eye that a surgeon is currently focusing on and can cause the diagnostic device to focus on the location. In some cases, a picture-in-picture image 460 (e.g. a picture-in-picture diagnostic image) can be overlaid on the main surgical window 402.

The surgical suite optimization engine can also receive surgical procedure data from a surgical console, a surgical guidance application, or other components in the surgical suite and can cause the GUI to display the surgical procedure data. For example, the GUI 400 can display a current procedure stage 420 and/or current procedural step 422.

As explained above, the surgical suite optimization engine can analyze an image of anatomy and digitally process the image to focus on certain anatomy, highlight certain features, etc. In some cases, the surgical suite optimization engine can process a variety of distinct surgical views that each include various processed data (e.g. a view that focuses on a macula, a view that focuses on a retinal tear, etc.) and the GUI 400 can display an interactive stack of surgical views 424. A surgical team member can select a particular surgical view from the interactive stack of surgical views 424 and the selected view can be displayed in the main surgical view window 402.

The GUI 400 can also include a variety of menu items 426, 428, 430, 432, 434, 436 for interacting with the surgical suite optimization engine or other components in the surgical suite. For example, the GUI 400 can include a surgical plan menu item 426 for interacting with a surgical planning application, surgical plan preferences, etc. The GUI 400 can also include a surgical practice management application 428, a technical support contact menu 430, etc. Also, the GUI 400 can include control menus such as a supplemental optics/overlay menu 432, a display position menu 434, a diagnostic device control menu 436, etc.

The GUI 400 can also include a variety of icons for controlling aspects of the display such as an Information Icon 438, a color adjustment icon 440, a camera adjustment icon 442, a monitor adjustment 444, a screen recording 446, an input source icon 448, a screen layout icon 450, a surgical step icon 452, etc.

A wide variety of common approaches can be employed for interacting with the GUI 400 displayed on a heads-up display, e.g. a mouse, a touchpad, etc. Additionally, the heads-up display can include a touchscreen and the GUI 400 can be interacted with via the touchscreen. However, maintaining a sterile environment can be important in a surgical suite and a surgeon may already be using both hands for manipulating tools and his feet with foot pedals. Therefore, contact-less interaction with the GUI 400 can be helpful. As explained above, in some cases, the surgical suite optimization engine includes a voice control module for recognizing voice commands for interacting with the GUI 400.

Additionally, in some cases, the surgical suite optimization engine can employ gaze-tracking to interact with the GUI 400. For example, surgical glasses used to view a stereoscopic image can include an eye tracking mechanism (e.g. a camera, one or more accelerometer etc.) that can detect eye position, movement of gaze, duration of focus, etc. and the GUI 400 can be interacted with using the detected eye/gaze position.

Some embodiments of gaze-tracking involve placing two or more accelerometers into the lightweight glass frames. These glasses can facilitate positioning of a digital pointer to on-screen menus and activating a function of the menu after the pointer remains on the menu for a threshold period of time or after verifying selection with a second selection function (e.g., foot pedal, finger embedded with sensor selection technology, voice, etc.). The digital pointer allows selection assistance via x or y-axis movements for navigating through menus and selecting preferred image or options. In some cases, the accelerometers determine when surgeon's gaze remains on a particular part of the GUI 400 for a threshold time (e.g. two seconds) and cause a pointer to appear on the GUI 400. In some cases, once the pointer is displayed, a menu will pop up to confirm the selection.

Figure 4B:
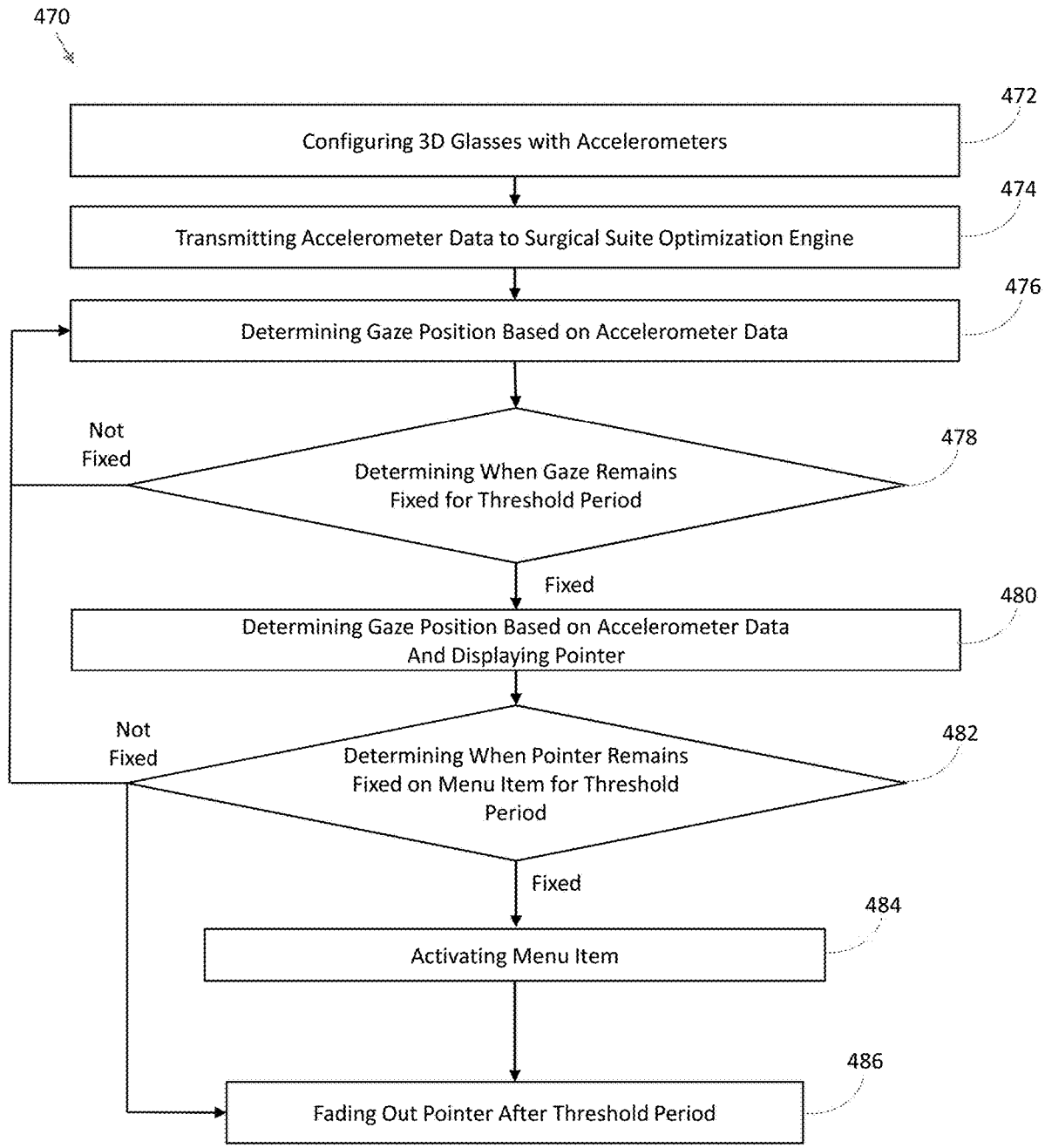
FIG. 4B illustrates a method of gaze-enabled control of a graphical user interface.

FIG. 4B illustrates a method 470 of gaze-enabled control of a graphical user interface. The method involves configuring three-dimensional glasses with accelerometers 472 transmitting accelerometer data to surgical suite optimization engine 474, and determining gaze position based on accelerometer data 476. Next, the method 470 involves determining when gaze remains fixed for threshold period 478 (e.g. two seconds). When the threshold is not reached, the method 470 continues to determining gaze position based on accelerometer data 476. When the threshold gaze fixture is reached, the method 470 involves determining gaze position based on accelerometer data and displaying a pointer that follows the gaze 480. Next, the method 470 involves determining when the pointer remains fixed on menu item for an additional threshold period (e.g. two seconds, three seconds) 482. When gaze fixture on the menu item does not reach the additional threshold, the method 470 continues to determining gaze position based on accelerometer data 476. When gaze fixture on the menu item reaches the additional threshold, the method 470 involves activating the menu item 484 and fading out pointer after a further threshold period 486.

The GUI 400 described herein is one example of a wide variety of interfaces that can be used for conducting surgical procedures. The benefits of such a GUI is even increased by the surgical suite optimization engine. As explained above, in response to receiving signals from other surgical components, the surgical suite optimization engine can perform a variety of actions to optimize the ophthalmic surgery suite.

Adjusting Display Settings

An example of the surgical suite optimization engine performing an action to optimize the ophthalmic surgery suite involves a surgical console transmitting procedure data and the surgical suite optimization engine adjusting display settings in the heads-up display based on the procedure data.

Figure 5A:
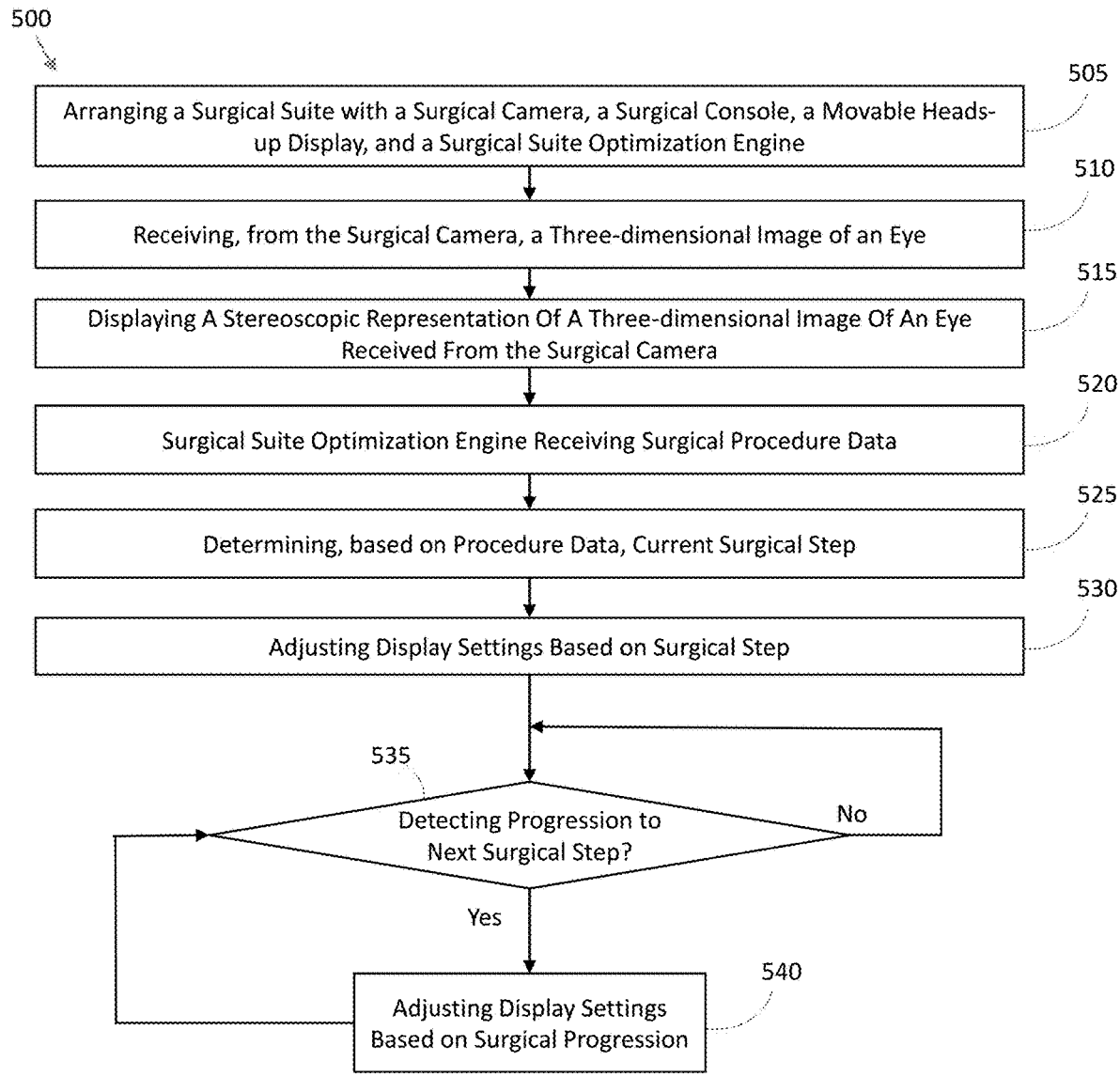
FIG. 5A illustrates a method of adjusting display settings based on surgical progression.
Figure 5B:
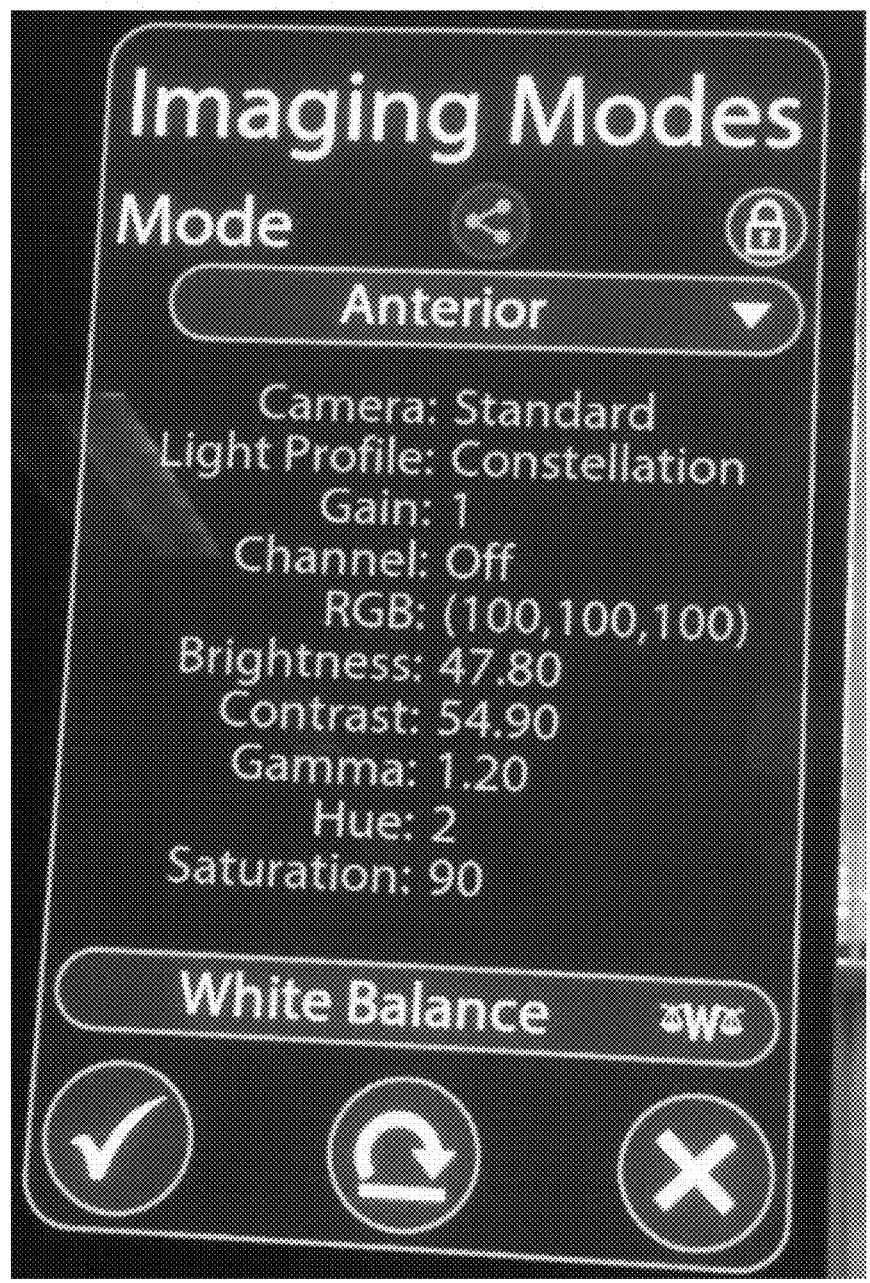
FIGS. 5B-5E illustrate examples of display settings for various steps of an ophthalmic procedure.
Figure 5C:
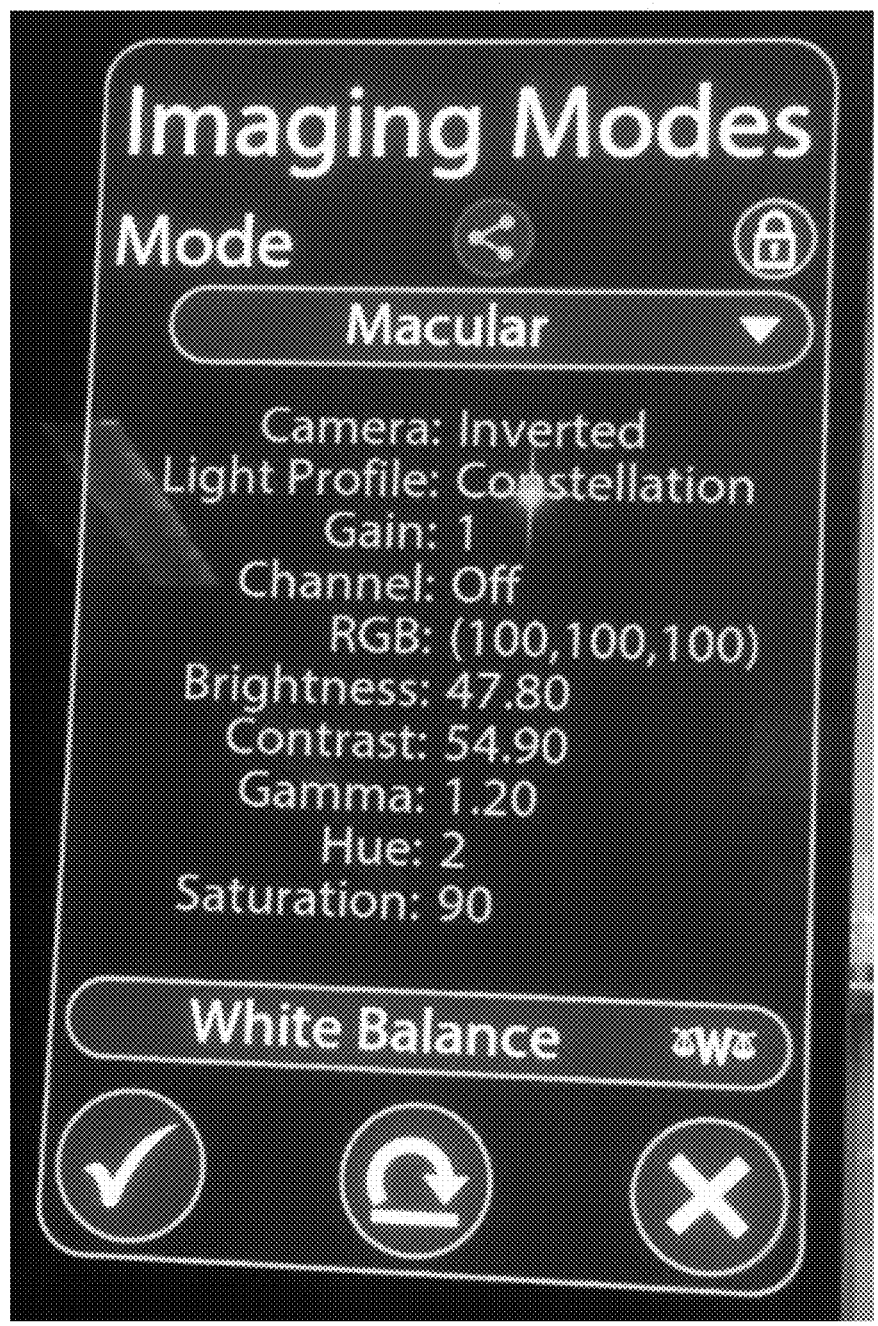
Figure 5D:
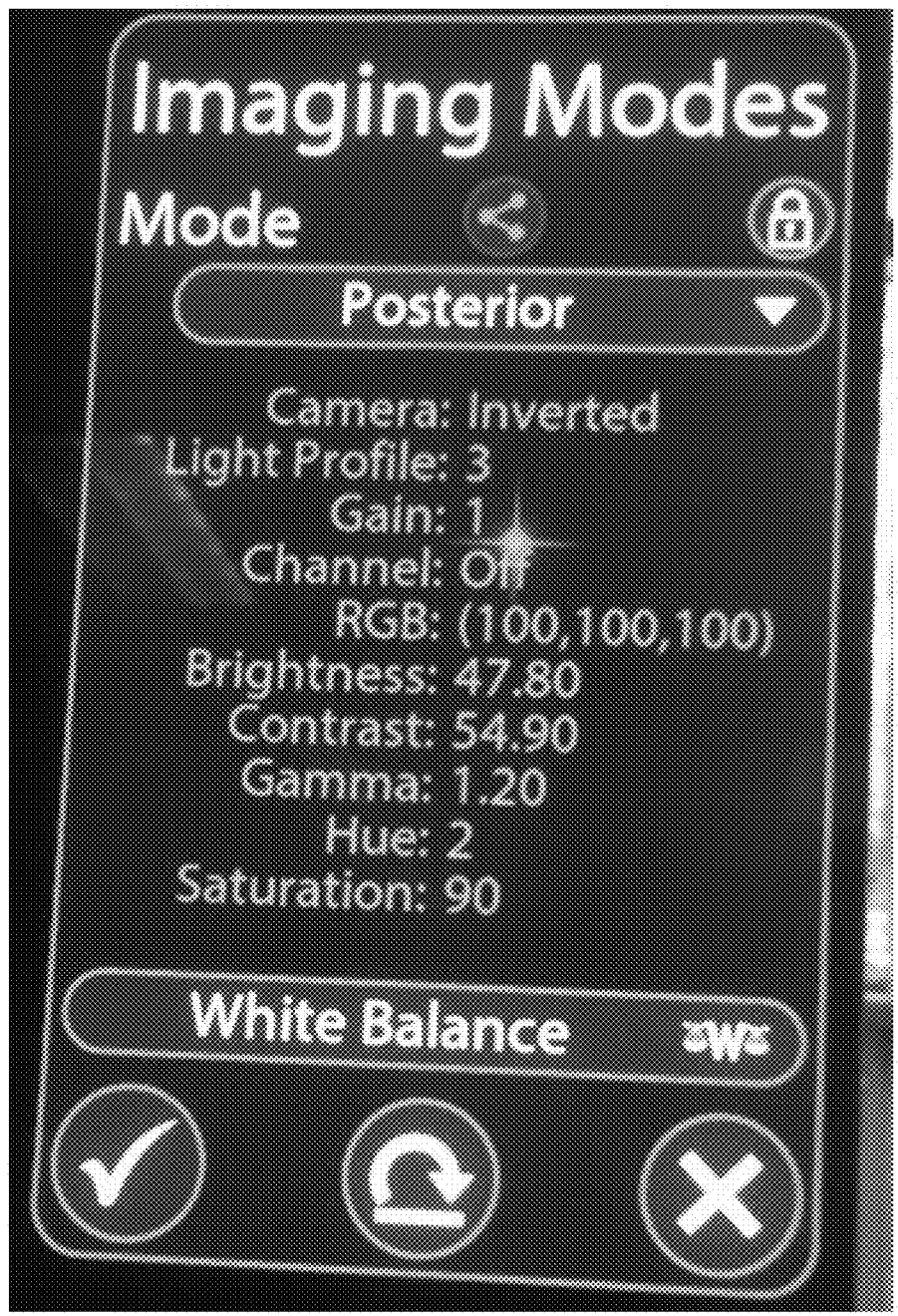
Figure 5E:
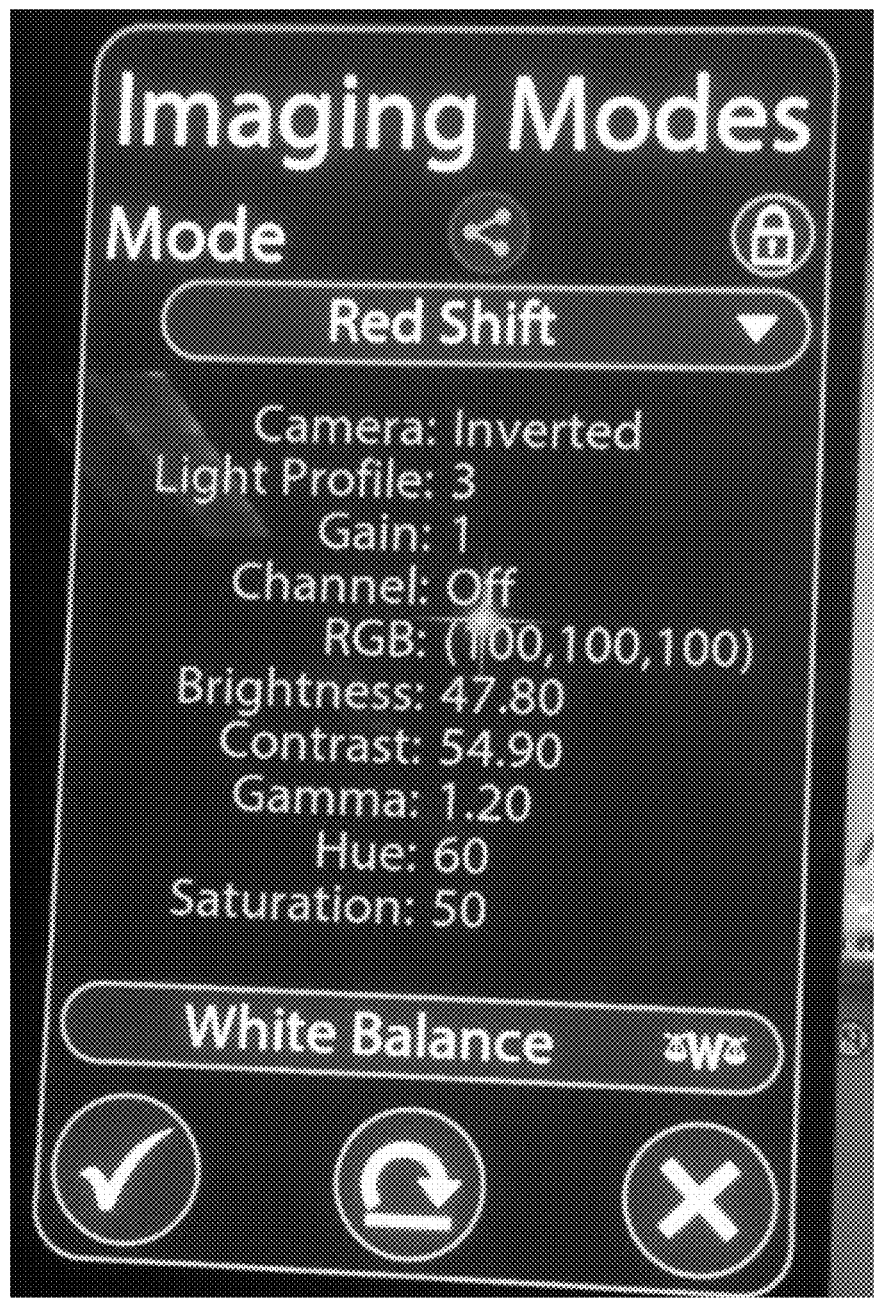

FIG. 5A illustrates a method 500 of adjusting display settings based on surgical progression. The method 500 involves arranging a surgical suite with a surgical camera, a surgical console, a movable heads-up display, and a surgical suite optimization engine 505. Next, the method 500 involves receiving, from the surgical camera, a three-dimensional image of an eye 510 and displaying a stereoscopic representation of a three-dimensional image of an eye received from the surgical camera 515.

The surgical suite optimization engine can be communicatively coupled with the surgical console and the method 500 can involve the surgical suite optimization engine receiving surgical procedure data 520 from the surgical console. To enhance the display, the method 500 can involve determining, based on procedure data, current surgical step 525 and adjusting display settings based on surgical step 530. Next, the method 500 can involve detecting progression to next surgical step 535 and adjusting display settings based on surgical progression 540. FIGS. 5B-5E illustrate examples of display settings for various steps of an ophthalmic procedure.

Optimizing Stereopsis

In some cases, the surgical suite optimization engine can receive information about steps/stages in a surgical procedure and can optimize stereopsis for surgical staff viewing the displayed stereoscopic representation of a three-dimensional image of eye anatomy in response to a change in the phase of a surgical procedure and/or procedure type, a manual command, a user preference, etc.

Using a HDR camera enables a high quality, three-dimensional image of patient anatomy. Also, a stereoscopic effect and/or hypersteropsis can be achieved to provide the surgical staff to perceive relative depth in the display of the patient anatomy. These effects are a function of several parameters including distance between cameras and the distance of the observing surgeon's eyes in relation to the display. Also, individual surgeons may prefer more or less stereopsis. Individual surgeons may also want the stereopsis modified for different procedure types or different surgical steps within a procedure type. In some embodiments of the present technology, a heads-up display can be mounted to a movable mechanism that moves the heads-up display to dynamically adjust the distance of the observing surgeon's eyes in relation to the display.

Figure 6A:
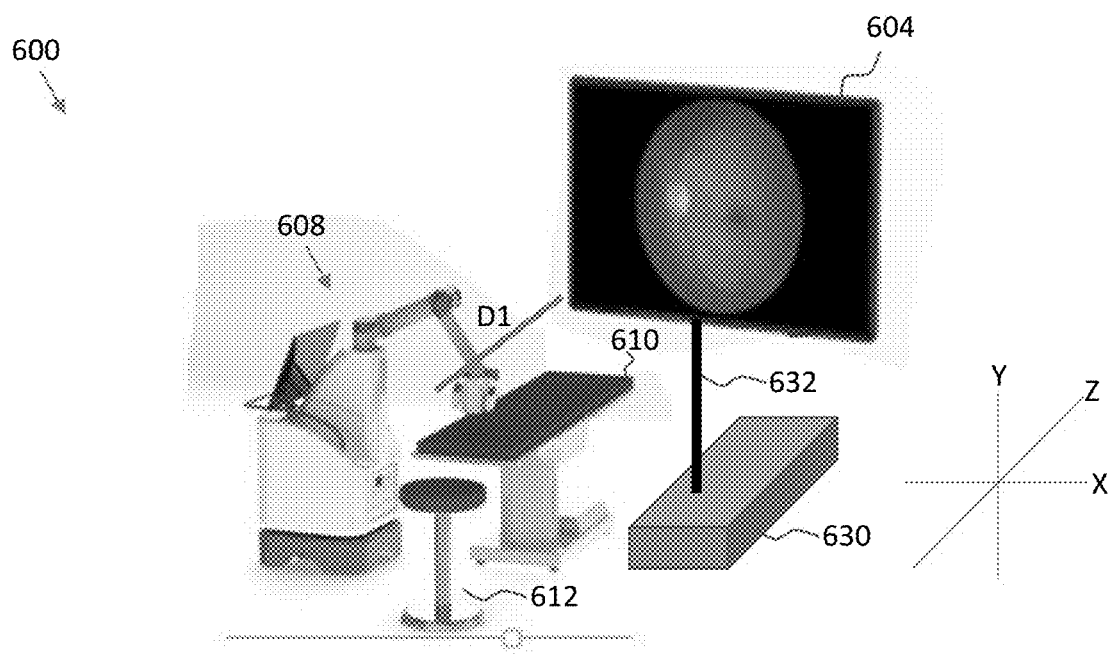
FIGS. 6A and 6B illustrate a system for adjusting the distance of a heads-up display in relation to an observation point.
Figure 6B:
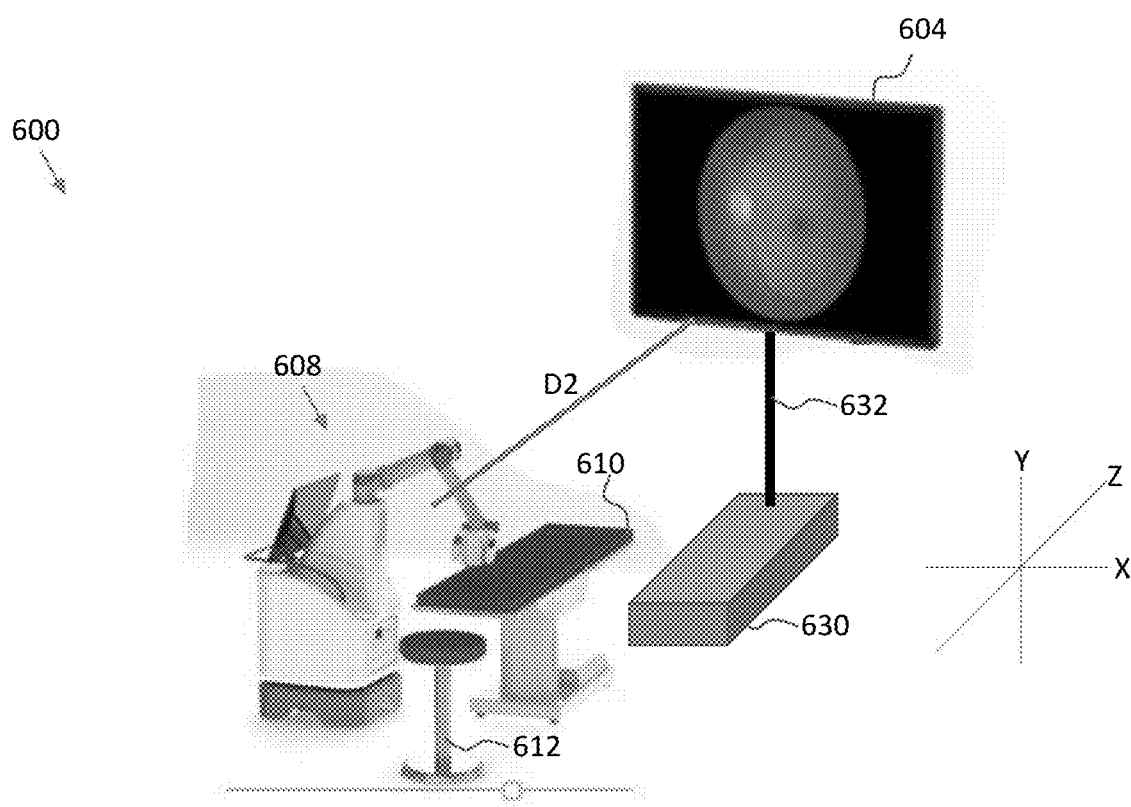

FIGS. 6A and 6B illustrate a system 600 for adjusting the distance of a heads-up display 604 in relation to an observation point according to some embodiments of the present technology. The system 600 includes a surgical camera 608 positioned above a patient table 610. The surgical camera 608 is configured to capture a three-dimensional image of patient anatomy for a patient on the patient table 610 and transmit the image data to a heads-up display 604. A surgeon can be positioned on a stool 612, for example, near the head of the patient and perform a procedure on the patient using a surgical console (not shown).

As shown, the heads-up display 604 is floor-mounted with a mount base 630 and a support member 632. The mount base 630 can include an adjustment mechanism for moving the support member in a z-direction to change the distance between the heads-up display 604 and the surgeon. For example, the mount base 630 can employ electro-mechanic solutions such as linear actuators, screw-drive mechanisms as well as hydraulics, pneumatics, etc. Also, the support member 632 can be adjusted in the x- and y-directions. For example, the support member 632 can include a vertical telescopic member that can be adjusted in the y-direction and a horizontal adjustment member (not shown) attached to the back of the heads-up display 604 that can be adjusted in the x-direction.

Although a floor-mounted system is illustrated, those with ordinary skill in the art having the benefit of the present disclosure will readily appreciate that a wide variety of mounting and adjustment systems can be employed to achieve the stereoscopic optimization benefit described herein. For example, a ceiling mount may have advantages based on a greater range of unobstructed movement compared to a floor mounted configuration. Also, although an ophthalmic surgery system is described, those with ordinary skill in the art having the benefit of the present disclosure will readily appreciate that a wide variety of procedure types can benefit from the stereoscopic optimization described herein. For example, otorhinolaryngology procedures, neurosurgeries, neck surgeries, back surgeries, internal chest surgeries, joint surgeries, ligament surgeries, muscle surgeries, bone surgeries, organ surgeries, and dental surgeries would particularly benefit.

In some cases, the heads-up display 604 can present an interactive graphical user interface (GUI) with interactive elements for allowing a user to configure a display position program. For example, the display position program can allow the surgical staff to manually adjust the position of the display relative to the surgeon, enter surgeon preferences, enable adjustment of the display distance based on a type of procedure, a step or phase in the procedure, etc. The heads-up display 604 can also include a surgical suite optimization engine (not shown) which can receive surgical procedure data (e.g. from the surgical console) that describes steps and/or phases of a particular procedure. For example, in cataract surgeries, the surgical procedure data can describe a capsulorhexis step, a phacoemulsification step, an irrigation/aspirating step, etc. and in retinal surgeries, the procedure data can describe an ILM peel step, a vitrectomy step, a Scleral buckle step, etc. Likewise, in a combination anterior/posterior procedure, the procedure data can describe a Cataract Phase and a Retinal Phase. The surgical suite optimization engine can also include a database of optimal display positions based on surgical steps/phases and a database that stores surgeon preferences.

The surgical suite optimization engine can receive surgical procedure data, monitor surgical progression (e.g. via feedback from the surgical console), detect one or more changes in surgical phase and/or surgical step, determine an optimal distance, and perform the action of moving the heads-up display 604 based on procedure phase/step and surgeon preferences. For example, moving the heads-up display 604 can involve the Surgical Suite Optimization engine transmitting an instruction that causes one or more actuator to move the heads-up display.

In FIG. 6A, the heads-up display 604 is located a distance D1 away from the position of the surgeon. FIG. 6B illustrates the system 600 after the surgical suite optimization engine detects a change in surgical step/phase and moves the heads-up display 604 to a distance D2 away from the position of the surgeon to optimize the stereoscopic effect for the current step/phase of the procedure.

Figure 6C:
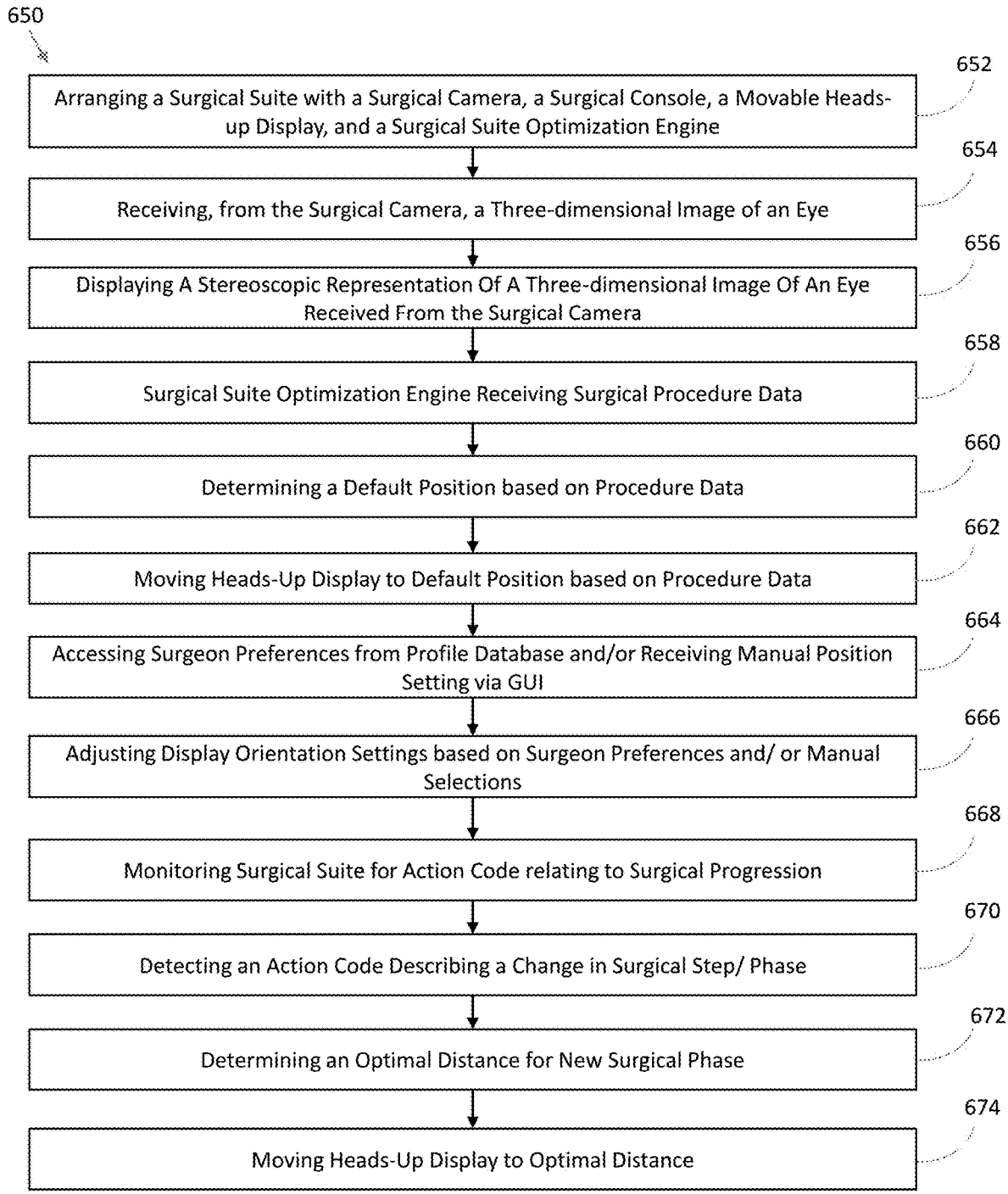
FIG. 6C illustrates a method of optimizing stereopsis for surgical staff viewing the displayed stereoscopic representation of a three-dimensional image of eye anatomy in response to a change in the phase of a surgical procedure and/or procedure type.

FIG. 6C illustrates a method 650 of optimizing stereopsis for surgical staff viewing the displayed stereoscopic representation of a three-dimensional image of eye anatomy in response to a change in the phase of a surgical procedure and/or procedure type. Initially, the method 650 involves arranging a surgical suite with a surgical camera, a surgical console, a movable heads-up display, and a surgical suite optimization engine 652.

Next, the method 650 involves receiving, from the surgical camera, a three-dimensional image of an eye 654 and displaying a stereoscopic representation of a three-dimensional image of an eye received from the surgical camera 656 on the heads-up display. The method 650 proceeds by the surgical suite optimization engine receiving surgical procedure data 658. For example, a surgical console can transmit surgical procedure data to the surgical suite optimization engine. Also, in some cases, surgical procedure data can be generated by one or more surgical guidance applications, a pre-operative surgical planning application, etc.

In some cases, a method 650 of optimizing stereopsis can involve the surgical suite optimization engine determining an initial default position for the heads-up display based on the procedure data 660, e.g. by referencing a database describing optimal distances based on procedure, analyzing historical surgical data describing best practices, etc. Next, the method 650 can involve the surgical suite optimization engine transmitting an instruction to a display positioning system (e.g. movable base, actuating arm, etc.) and moving the heads-up display to default position based on procedure data 662.

Next, the method 650 involves accessing surgeon preferences from profile database and/or receiving manual position setting via a GUI 664, adjusting display orientation settings based on surgeon preferences and/or manual selections 666, and monitoring surgical suite for action code relating to surgical progression 668. In some cases, a surgical console communicatively coupled with the surgical suite optimization engine transmits an action code (or other signal) when a change in the surgical step/phase, e.g. automatically when a new instrument is used, after receiving manual input from surgical staff, after recognizing a speech command from the surgical staff, etc. The method 650 involves detecting an action code describing a change in surgical step/phase 670, determining an optimal distance for the heads-up display for new surgical phase to optimize stereopsis 672, and moving heads-up display to optimal distance 674.

Image Auto-Centration and Auto-Coaxial Illumination for Optimal Red Reflux

Another example of the surgical suite optimization engine performing an action to optimize the ophthalmic surgery suite involves automatically centering surgical camera with a patient's eye. In a three-dimensional surgery system, the surgical camera should remain centered on the pupil such that the eye can be presented centrally and fully on the heads-up display without vignettes and to ensure optimal lighting conditions, i.e. Red Reflex. However, as a patient's head and/or eye moves or is repositioned by the surgeon, the patient's eye can drift outside of the surgical camera's image center causing surgical staff to reposition the patient or the camera.

Some embodiments of the present technology involve the surgical camera mounted on a positioning mechanism and involve the surgical camera and/or the surgical suite optimization engine configured to track a position of the eye (e.g. using anatomical registration). The positioning mechanism can be, for example, a robotic arm, a gimbal, a linear positioning system, etc. Further, the surgical camera and/or the surgical suite optimization engine can include control system that can control the positioning mechanism to reposition the surgical camera to remain centered on the eye to ensure centration on the viewing display and to ensure that light source(s) to always be substantially perpendicular to the pupil. Tracking the eye and controlling the positioning mechanism can ensure centration and bright illumination conditions, e.g. optimized red reflex.

Further, in some embodiments, color and light post-processing imaging algorithms may also be employed by the surgical suite optimization engine to optimize red reflex images. Also, some specific light wavelengths can be selected/filtered that better penetrate media opacities of the cornea, crystalline lens, or vitreous that may be detrimental to establishing an optimized red reflex. Similarly, adaptive optics may help eliminate aberrations that can diminish a bright red reflex and auto-focus in one or multiple zones.

Figure 7:
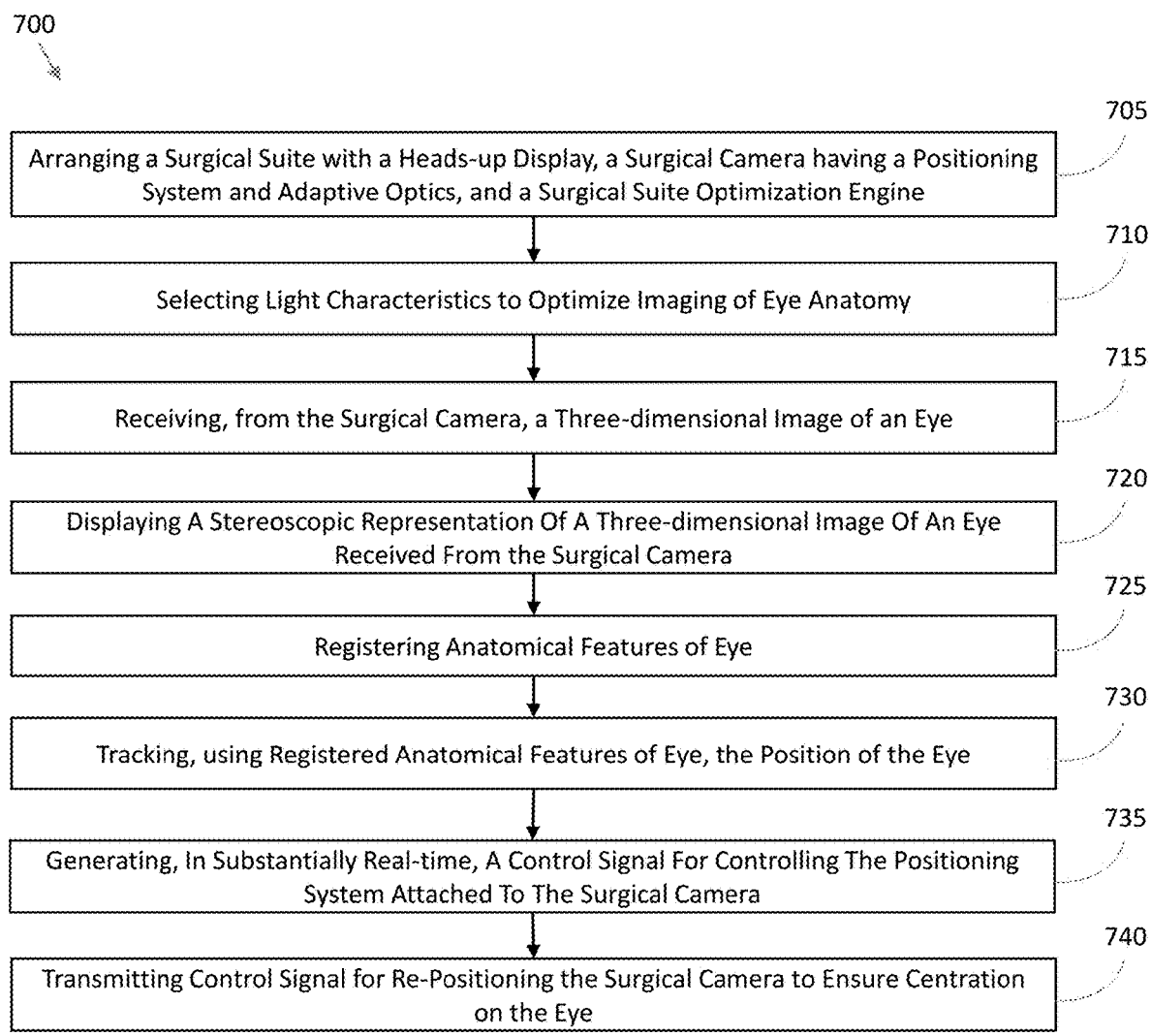
FIG. 7 illustrates a method of ensuring centration of a surgical camera on an eye.

FIG. 7 illustrates a method 700 of ensuring centration of a surgical camera on an eye according to some embodiments of the present technology. The method 700 involves arranging a surgical suite with a heads-up display, a surgical camera having a positioning system and adaptive optics, and a surgical suite optimization engine 705. In some cases, adaptive optics are selected to eliminate aberrations in the cornea, crystalline lens, vitreous, etc. that may inhibit optimal imaging of the anterior surfaces of the eye such as the anterior capsule surface, posterior capsule surface, etc. Elimination of the opacities combined with image centration can result in optimal light conditions and anatomical clarity. The method 700 can further include selecting light characteristics for the surgical camera to optimize imaging of eye anatomy 710. For example, selecting light characteristics can include selecting wavelengths that better penetration of media opacities of the cornea, crystalline lens, vitreous, etc., selecting wavelengths that are safer to the human eye, eliminating particular region (e.g. blue) of the spectrum, etc.

Next, the method 700 can involve a surgical suite optimization engine receiving, from the surgical camera, a three-dimensional image of an eye 715 and displaying, on the heads-up display, a stereoscopic representation of a three-dimensional image of an eye received from the surgical camera 720. The method 700 also involves the surgical suite optimization engine registering anatomical features of eye 725 and tracking, using registered anatomical features of eye, the position of the eye 730. As the surgical suite optimization engine tracks the position of the eye, the method 700 can involve the surgical suite optimization engine generating, in substantially real-time, a control signal for controlling the positioning system attached to the surgical camera 735 and transmitting control signal for re-positioning the surgical camera to ensure centration on the eye 740.

Adjusting Diagnostic Device

Another example of the surgical suite optimization engine performing an action to optimize the ophthalmic surgery suite involves the surgical suite optimization engine enhancing diagnostic visualization of anatomy and pathology. Many of the anatomical aspects of the eye are transparent, thus playing a role in passing light through the human eye optical system to the neuro-sensory retina. To distinguish these tissues from similarly transparent membrane pathologies is challenging even during pristine conditions. These clear tissues often become opacified or hazy including the cornea, crystalline human lens and capsule, and vitreous opacities and hemorrhage. These sub optimal optical conditions in inherently clear structures make surgery challenging and limit optimal surgical precision and subsequent patient outcomes. To optimize visualization of eye anatomy and pathology, some embodiments of the present technology involve digital diagnostic and supplementary images that can help distinguish anatomical and pathological components.

For example, in some cases the Surgical Suite Optimization engine can receive imagery from both a surgical camera and a diagnostic device, e.g. an Optical Coherence Tomography (OCT) device; digital endoscopic cameras; laser speckle flowgraphy devices, ultrasound/echograph devices, wavefront and laser devices, light interrogation/reflectance devices, etc. The Surgical Suite Optimization engine can combine the imagery, blend diagnostic views with camera views, etc. Further, the Surgical Suite Optimization engine can apply digital enhancement technologies to subtract aberrations from the optical system. For example, in some cases the Surgical Suite Optimization engine can apply adaptive optics technology to automatically strip aberrations and sharpen the clarity of the view for the surgeon.

A wide variety of application for diagnostics and adaptive optics can be applied to enhance a surgical procedure; however, an illustrative example involves corneal inlay surgery for addressing presbyopia. Presbyopia affects more patients than any other age related disease process. A variety of refractive and/or mechanical polymers have been designed to be placed intra-cornea to adjust for refractive error and/or presbyopia. The inlay performance and ease of installation are a function of imaging and diagnostics available to the surgeon. The surgical camera, heads-up display, and surgical suite optimization engine pf the present technology provides surgeons with an excellent platform for optical and digital guidance for minimally invasive Corneal Refractive/Presbyopia correction. In some cases the surgical suite optimization engine can define diagnostic settings and perform digital image post processing with color attribute filtering and/or image enhancement technology such as adaptive optics and can make the inlay procedure more precise for the ophthalmic surgeon. These technologies can provide complementary images to the traditional optical view to provide more informed decision making for the surgeon.

Figure 8:
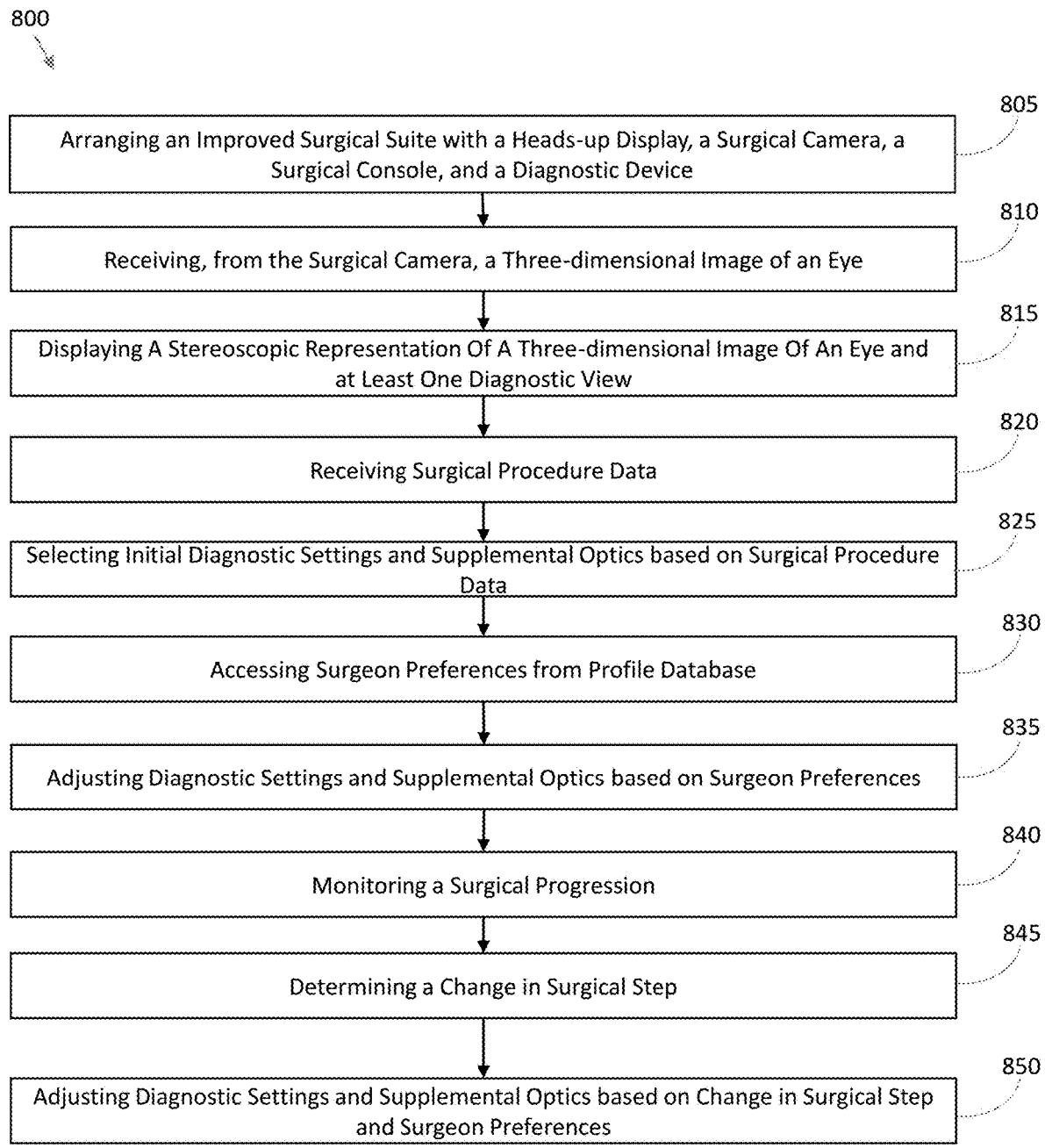
FIG. 8 illustrates a method of enhancing diagnostic visualization for surgical staff viewing a stereoscopic representation of a three-dimensional image of eye anatomy.

FIG. 8 illustrates a method 800 of enhancing diagnostic visualization for surgical staff viewing a stereoscopic representation of a three-dimensional image of eye anatomy. Initially, the method 800 involves arranging a surgical suite with a heads-up display with a surgical suite optimization engine, a surgical camera, a surgical console, and a diagnostic device (e.g. an Optical Coherence Tomography (OCT) device; digital endoscopic cameras; laser speckle flowgraphy devices, ultrasound/echograph devices, wavefront and laser devices, light interrogation/reflectance devices, etc.) 805.

Next, the method 800 involves receiving, from the surgical camera, a three-dimensional image of an eye 810 and displaying a stereoscopic representation of a three-dimensional image of an eye and at least one diagnostic view 815 on the heads-up display. The method 800 proceeds by the surgical suite optimization engine receiving surgical procedure data 820. For example, a surgical console can transmit surgical procedure data to the surgical suite optimization engine. Also, in some cases, surgical procedure data can be generated by one or more surgical guidance applications, a pre-operative surgical planning application, etc.

Next, the method 800 involves selecting initial diagnostic settings and supplemental optics based on surgical procedure data 825, accessing surgeon preferences from profile database 830, adjusting diagnostic setting and supplemental optics based on surgeon preferences 835, and monitoring surgical suite for action code relating to surgical progression 840. In some cases, a surgical console communicatively coupled with the surgical suite optimization engine transmits an action code (or other signal) when a change in the surgical step/phase, e.g. automatically when a new instrument is used, after receiving manual input from surgical staff, after recognizing a speech command from the surgical staff, etc. The method 800 involves detecting an action code describing a change in surgical step/phase 845 and adjusting diagnostic settings and supplemental optics based on change in surgical step and surgeon preferences 850. In some cases, adjusting diagnostic settings can involve moving the diagnostic device (e.g. on a robotic arm) to aim the diagnostic device onto anatomy relevant to a surgical step/phase.

Dynamically Adjusting Anatomical Area of Focus, Anatomical Highlighting, and Graphical Overlays Another example of the surgical suite optimization engine performing an action to optimize the ophthalmic surgery suite involves dynamically adjusting anatomical area of focus, anatomical highlighting, and graphical overlays on or near the three-dimensional stereoscopic representation of patient's eye or in another location in the GUI displayed on the heads-up display.

The surgical suite optimization engine can be used with a surgical camera and heads up display to perform a large variety of ophthalmic procedures. Over the course of these procedures, it is beneficial for the surgical staff to observe a wide variety of areas of focus and specific anatomical features. In some embodiments of the present technology, the surgical suite optimization engine can monitor and/or anticipate surgical progression and can automatically focus on desired areas of focus and automatically highlight specific anatomical features by applying a variety of rules. Also wide variety of overlays can be used to optimize surgery. For example, pre-operative diagnostic images and planning tools can be overlaid on a surgical image of an eye to guide a surgeon in the placement of incisions, the alignment of an inter-ocular lens, etc. The surgical suite optimization engine of the present technology can also determine to adjust overlays by monitoring surgical progression and by applying rules for adjusting overlays.

In some embodiments of the present technology, the surgical suite optimization engine can apply pre-programmed rules for adjusting area of focus, anatomical highlighting, and/or graphical overlays. For example, the surgical suite optimization engine can receive surgical progression data from a surgical console and consult a display options database to access pre-programmed rules. In some cases, the Surgical Suite Optimization engine can also reference one or more surgical practice guidance application and access pre-programmed overlay template packages, e.g. used optimal by well-respected surgeons. Also, the surgical suite optimization engine can apply machine learning and artificial intelligence techniques and/or provide surgical data to a separate machine learning and artificial intelligence engine and request templates for dynamically adjusting anatomical area of focus, anatomical highlighting, and graphical overlays. For example, in some cases, the Surgical Suite Optimization engine can receive pre-programmed area of focus, highlighting and overlay templates created through machine learning and/or artificial intelligence that are determined to result in optimal patient outcomes.

Figure 9:
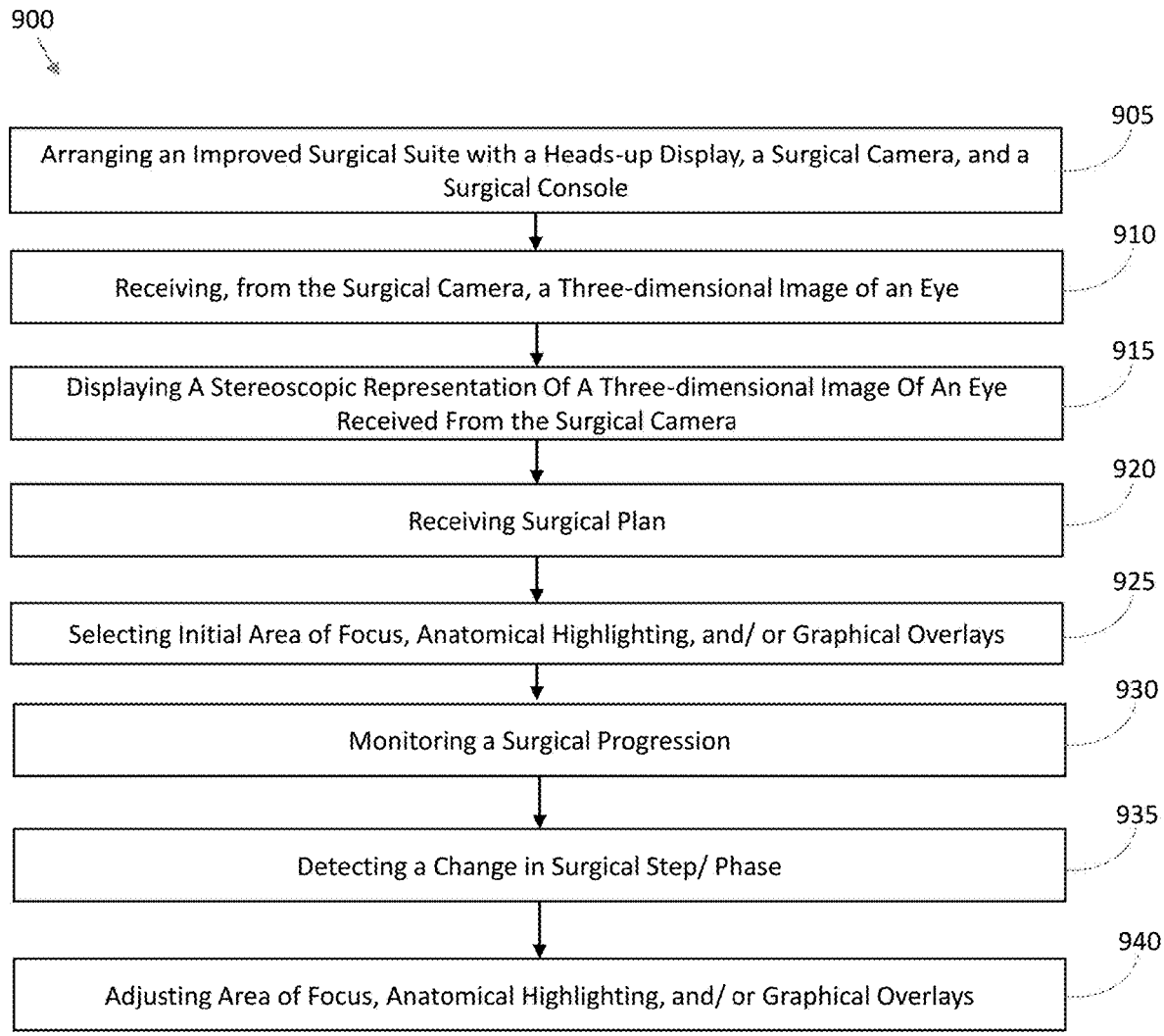
FIG. 9 illustrates a method of a surgical suite optimization engine dynamically adjusting anatomical area of focus, anatomical highlighting, and graphical overlays.

FIG. 9 illustrates a method 900 of a surgical suite optimization engine dynamically adjusting anatomical area of focus, anatomical highlighting, and graphical overlays according to some embodiments of the present technology. The method 900 involves arranging an improved surgical suite with a heads-up display, a surgical suite optimization engine, a surgical camera, and a surgical console 905. Next, the method 900 involves receiving, from the surgical camera, a three-dimensional image of an eye 910 and displaying a stereoscopic representation of a three-dimensional image of an eye received from the surgical camera 915. Further, the method 900 can involve receiving surgical plan 920. In some cases, a surgical plan can be received from a surgical console, a surgical guidance application, a machine learning and artificial intelligence engine, etc.

The method 900 further involves the surgical suite optimization engine selecting initial area of focus, anatomical highlighting, and/or graphical overlays 925, monitoring a surgical progression 930, detecting a change in surgical step/phase 935 and adjusting area of focus, anatomical highlighting, and/or graphical overlays 940 based on the new surgical step/phase.

Providing Surgical Alerts and Recommendations

Another example of the surgical suite optimization engine performing an action to optimize the ophthalmic surgery suite involves monitoring control limits and providing surgical alerts and recommendations.

In some cases, a surgical console (e.g. a surgical console configured for performing vitreoretinal surgery) can warn or prevent the user when certain thresholds are exceed to avoid potentially unsafe operations. For example, the use of low vacuum limits, low flow rates, low irrigation pressure, high power settings, extended power usage, power usage during occlusion conditions, failure to sufficiently aspirate viscoelastic prior to using power, excessively tight incisions, and combinations of the above actions may result in significant temperature increases at incision site and inside the eye, and lead to severe thermal eye tissue damage. A surgical console can enforce control limits to warn or prevent these and other potentially adverse conditions.

Figure 10:
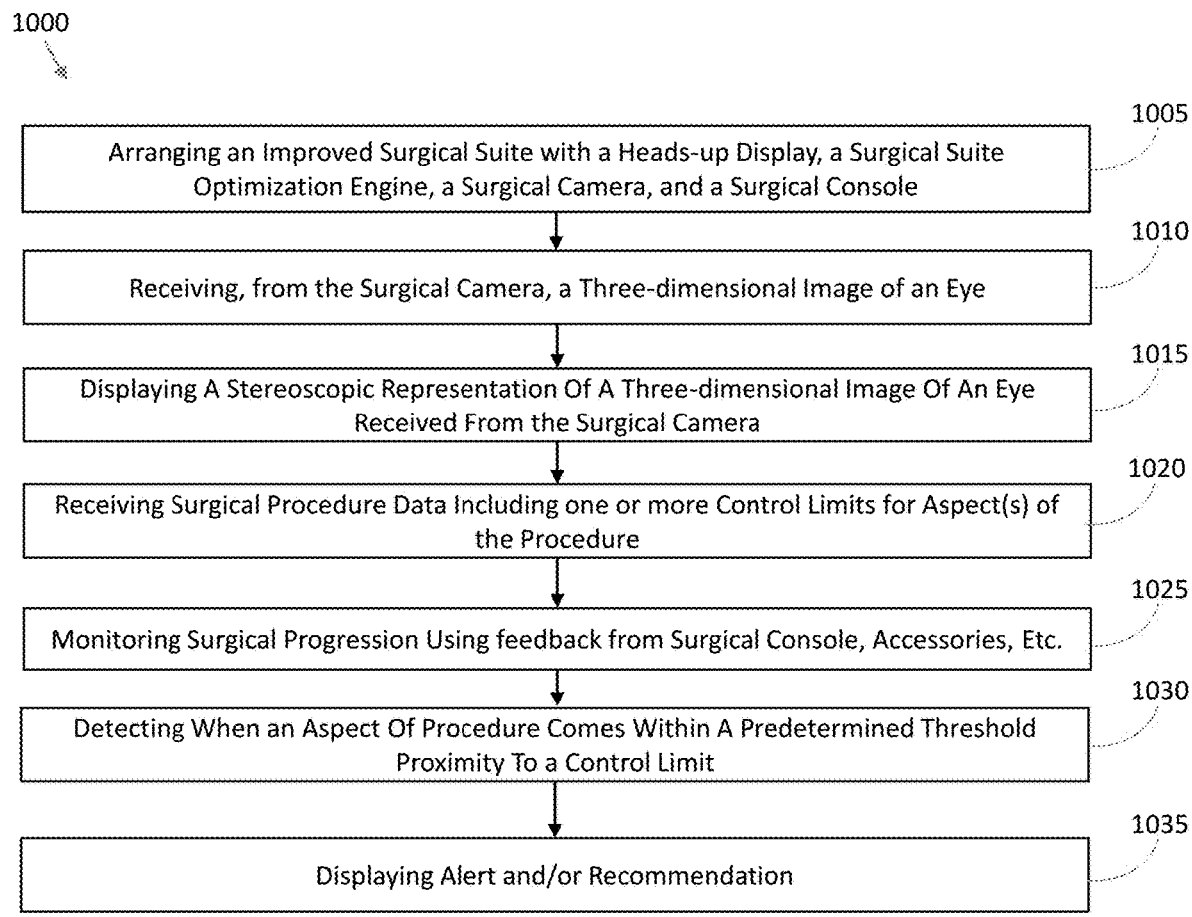
FIG. 10 illustrates a method of monitoring control limits and providing surgical alerts and recommendations.

FIG. 10 illustrates a method 1000 of monitoring control limits and providing surgical alerts and recommendations. The method 1000 involves arranging an improved surgical suite with a heads-up display, a surgical suite optimization engine, a surgical camera, and a surgical console 1005, receiving, from the surgical camera, a three-dimensional image of an eye 1010, and displaying a stereoscopic representation of a three-dimensional image of an eye received from the surgical camera 1015. In some cases, the surgical console can transmit surgical procedure data to the surgical suite optimization engine that includes one or more control limit threshold settings, e.g. a maximum advisable interocular pressure. In some other embodiments, an additional surgical practice guidance application can include one or more sources of control limit settings. For example, a surgical practice guidance application can include settings defined as optimal by well-respected surgeons, settings determined through machine learning and/or artificial intelligence as resulting in optimal patient outcomes, etc.

Next, the method 1000 involves receiving surgical procedure data including one or more control limits for aspect(s) of the procedure 1020 and monitoring surgical progression using feedback from surgical console, accessories, etc. 1025. For example, monitoring surgical progression can include monitoring intraocular pressure of a patient's eye by the surgical console. The method 1000 then involves detecting when an aspect of procedure comes within a predetermined threshold proximity to a control limit 1030 and causing the heads-up display to display an alert and/or recommendation on the heads-up display 1035.

Color Modulation for Laser Operation

Another example of the surgical suite optimization engine performing an action to optimize the ophthalmic surgery suite involves monitoring control limits and providing surgical alerts and recommendations. Poor visualization during surgical procedures can deter optimal surgical tasks and subsequently, limit optimal patient outcomes. However, the surgical suite optimization engine of the present technology can be used to adjust post-image capture image characteristics including color characteristics (e.g. saturation, contrast, gain, gamma, cast etc.) and light characteristics (e.g. exposure, contrast, blackpoint etc.) For example, while using a laser in retina surgery, there is typically a red aiming beam ~635 nm wavelength and a subsequent 532 nm treatment or photocoagulation beam. However, the red aiming beam can be difficult to see on the orange background of the human retina. This makes it challenging for the surgeon to optimize precise targeting of the treatment beam. Also, the treatment beam can create a "green flashback" as the beam strikes the targeted retina and may temporarily obscure the surgeon's vision and can compromise dark adaptation. Modulating color and/or light characteristics may be helpful to the surgeon to optimize visualization and patient outcomes. Accordingly, the surgical suite optimization engine can modulate pixel colors post-image capture. For example, the surgical suite optimization engine can accentuate the red aiming beam by adjusting specific tertiary color spectra to maximize red contrast. Modifying portions of the green spectrum opposite of 635 nm red (e.g. in Itten's color contrast circle) can maximize red contrast in the displayed image. Similarly, during green laser flashback the surgical suite optimization engine can neutralize green by temporarily reducing or eliminating the capability to display green. The surgical suite optimization engine can also truncate or modulate broad sections of spectra of primary (RGB) or secondary spectra (OPG) colors. Linking these color modulation techniques utilizing a graphics processing computer (GPU) of the surgical suite optimization engine provides a valuable integrated approach to optimizing surgeon performance.

In a specific example, when the Laser system software (e.g. a laser itself, a wireless footswitch coupled with the laser, the surgical console, etc.) communicates with the surgical suite optimization engine, the image modulations are coordinated. The state of the laser would invoke different modulation effects: in a first state ("Laser ready"), the surgical suite optimization engine optimizes the red aiming beam intensity and contrast; and in a second state ("Laser Firing"), the surgical suite optimization engine modulates or eliminates the green flashback. The surgical suite optimization engine can alternate these views instantaneously as the Laser is "aimed", then "fired", then "aimed" at a subsequent target and so on until all Laser spots are applied.

Figure 11A:
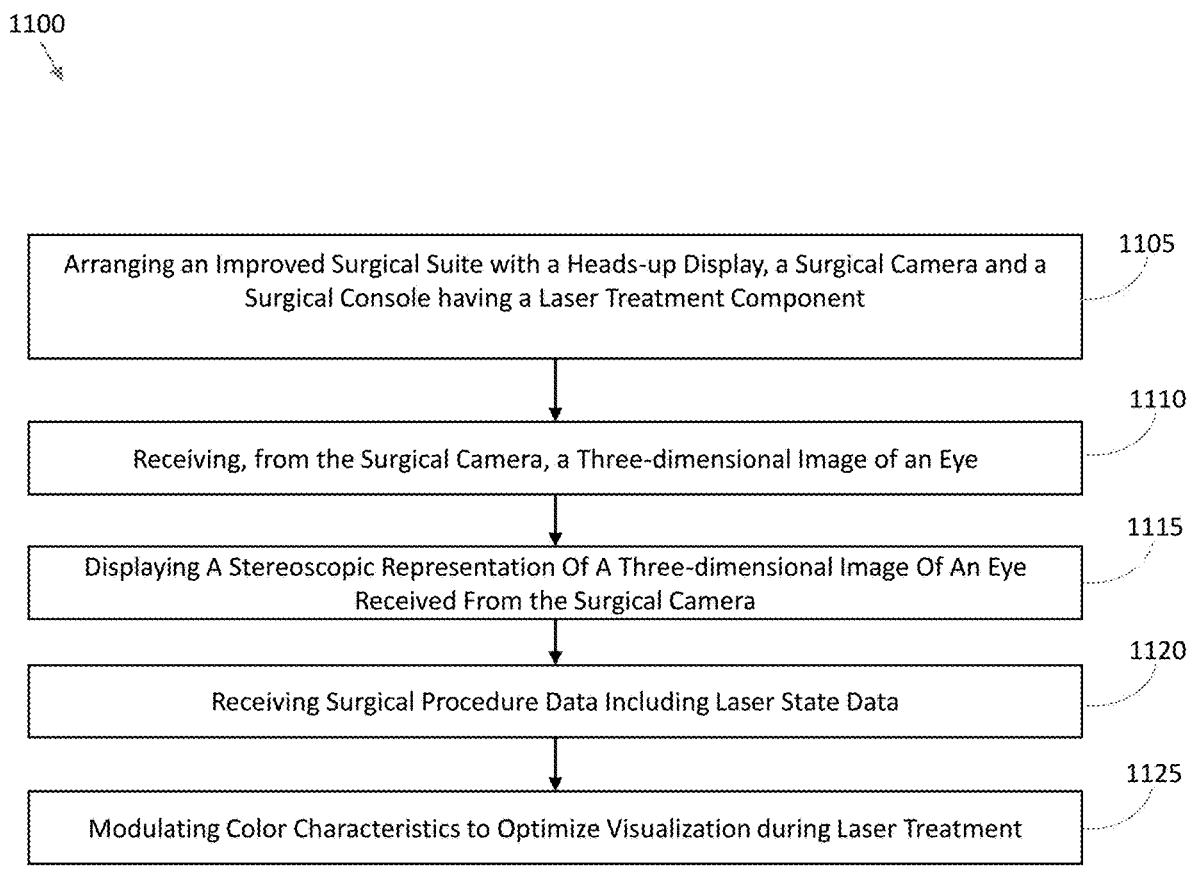
FIG. 11A illustrates a method of modulating color characteristics of a stereoscopic representation of a three-dimensional image of eye anatomy to optimize visualization during a laser treatment step of an ophthalmic procedure

FIG. 11A illustrates a method 1100 of modulating color characteristics of a stereoscopic representation of a three-dimensional image of eye anatomy to optimize visualization during a laser treatment step of an ophthalmic procedure. The method 1100 can involve arranging an improved surgical suite with a heads-up display, a surgical camera and a surgical console having a laser treatment component 1105, receiving, from the surgical camera, a three-dimensional image of an eye 1110, and displaying a stereoscopic representation of a three-dimensional image of an eye received from the surgical camera 1115. Next, the method 1100 can involve receiving surgical procedure data including laser state data 1120. For example, the laser state data can involve data indicating whether a laser used for photocoagulation of tissue in a retinal procedure is in an "aiming" state or a "firing" state. The laser state data can be transmitted from the surgical console, a laser module coupled to the surgical console, a stand-alone laser module, a wireless footswitch communicatively coupled with a laser module and configured to alternatively aim and fire the laser, etc.

Next, the method 1100 can involve modulating color characteristics to optimize visualization during laser treatment 1125. For example, modulating color characteristics to optimize visualization during laser treatment can involve performing digital signal processing to maximize red contract of the stereoscopic representation of the three-dimensional image of the eye when the laser treatment transitions from the emission of the treatment beam to the emission of the aiming beam and neutralizing a green flashback from a retina in the stereoscopic representation of the three-dimensional image of the eye when the laser treatment transitions from the emission of the aiming beam to the emission of the treatment beam. In some cases, the surgical suite optimization engine can include a dedicated graphical processing unit for performing digital signal processing.

Figure 11B:
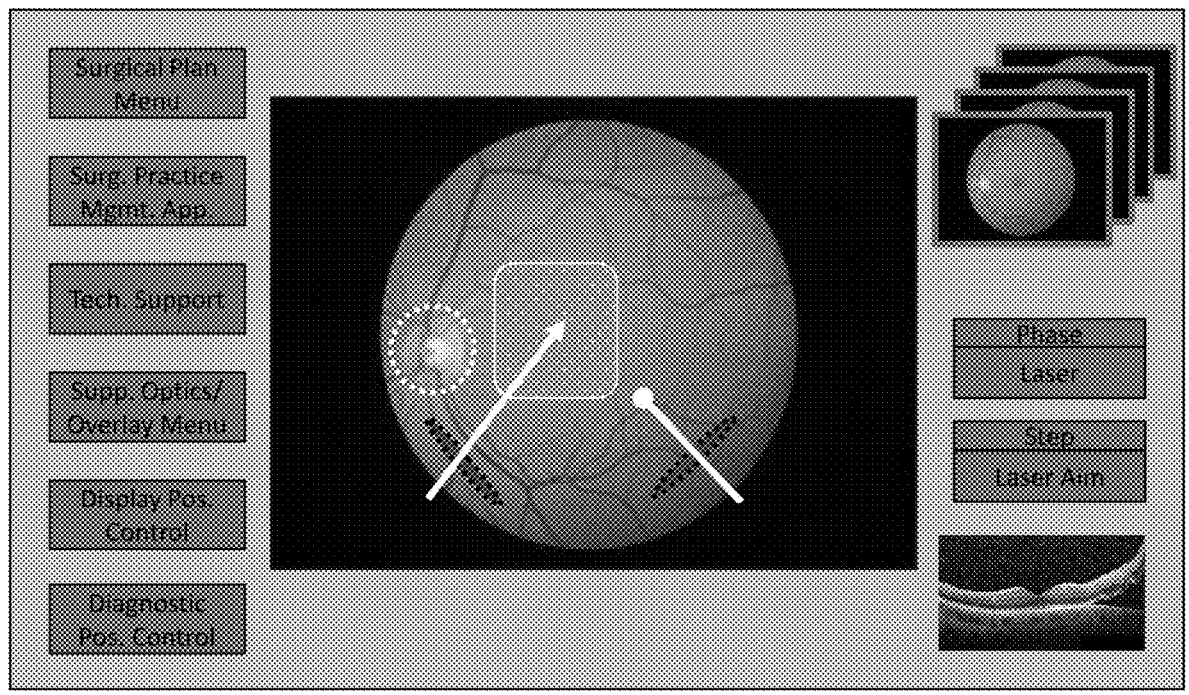
FIGS. 11B and 11C illustrate examples of graphical user interfaces showing optimized visualization for two laser states according to some embodiments of the present technology.
Figure 11C:
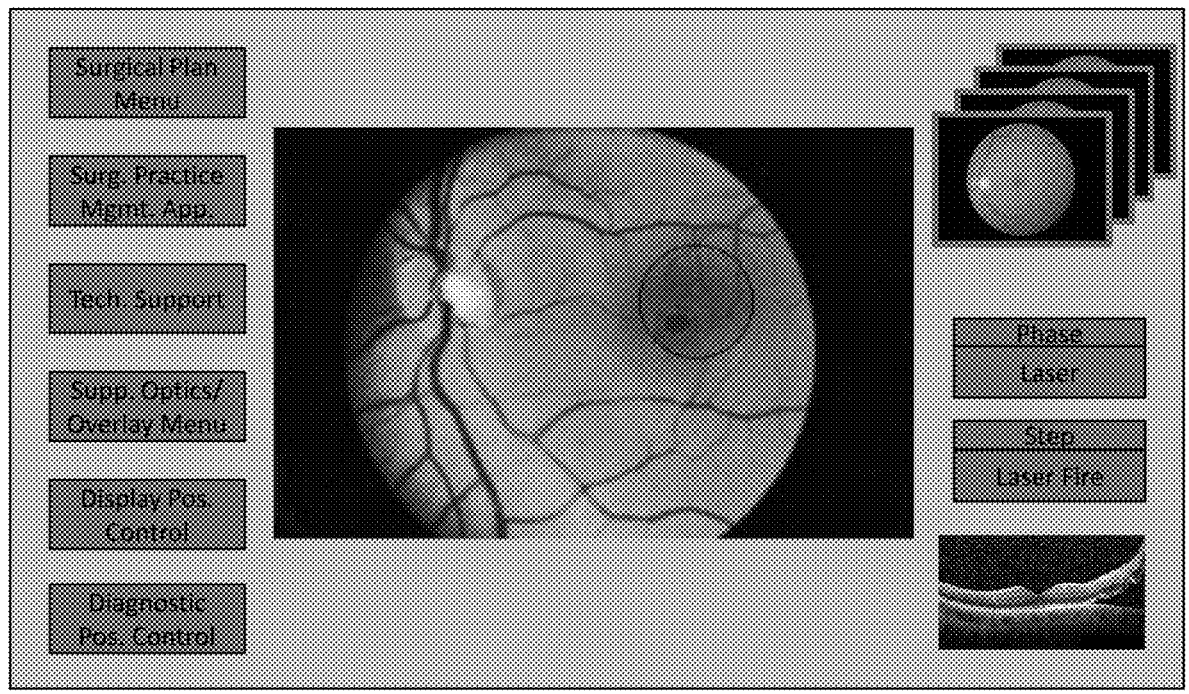

FIGS. 11B and 11C illustrate examples of graphical user interfaces showing optimized visualization for two laser states according to some embodiments of the present technology. As represented in FIGS. 11B and 11C, a graphical user interface (GUI) 1130 of a display dashboard includes a main surgical view window 1130 that displays a stereoscopic representation of a three-dimensional image of an eye received from the surgical camera. In FIG. 11B, the image of the eye is modulated toward red to maximize red contract during a laser aiming step. In FIG. 11C, the image of the eye is modulated toward green to neutralize green flashback during a laser firing step.

Automatically Contacting Support

Another example of the surgical suite optimization engine performing an action to optimize the ophthalmic surgery suite involves identifying a problem in the surgical suite and automatically initiating contact with a support professional to remedy the problem. One or more devices, accessories, software modules, etc. connected in a surgical suite can report errors to the surgical suite optimization engine and the surgical suite optimization engine can perform actions in response to the errors. For example, a surgical console can issue an error code in the event that one or more of the surgical console's components and/or software functions malfunctions or does not execute properly. In response to receiving the error code, the surgical suite can transcode the action code to a known format, if necessary, and determine to perform an action in response to the malfunction described in the action code. For example, when a component of a surgical console malfunctions, the surgical suite optimization engine can automatically initiate a call or video conference with a technical support team responsible for providing support for the surgical console. In another example, the surgical console can transmit an action code when a component is nearing its warranty end of life and the surgical suite optimization engine an automatically schedule a call with a sales representative responsible for maintaining a surgery practice's account. Those with ordinary skill in the art having the benefit of the present disclosure will readily appreciate that a wide variety actions can be supported by the surgical suite optimization engine in response to receiving error codes from components in the surgical suite.

Figure 12:
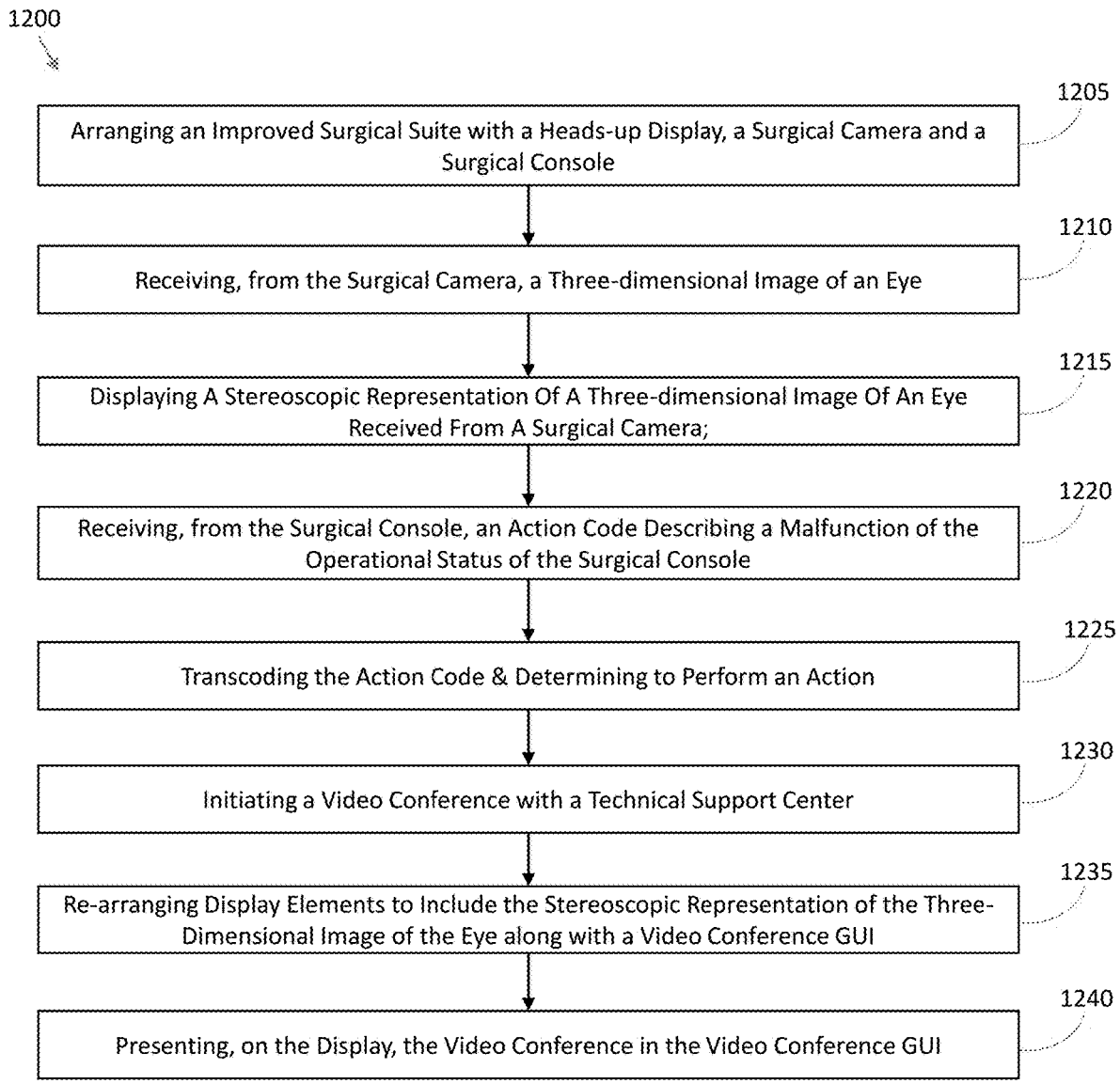
FIG. 12 illustrates a method of identifying a problem in the surgical suite and automatically initiating contact with a support professional to remedy the problem.

FIG. 12 illustrates a method 1200 of identifying a problem in the surgical suite and automatically initiating contact with a support professional to remedy the problem. The method 1200 involves arranging an improved surgical suite with a heads-up display, a surgical camera and a surgical console 1205, receiving, from the surgical camera, a three-dimensional image of an eye 1210, and displaying a stereoscopic representation of a three-dimensional image of an eye received from a surgical camera 1215. Next, the method 1200 can involve receiving, from the surgical console, an action code describing a malfunction of the operational status of the surgical console 1220, transcoding the action code and determining to perform an action 1225, and initiating a video conference with a technical support center 1230. Next, the method 1200 can involve re-arranging display elements to include the stereoscopic representation of the three-dimensional image of the eye along with a video conference GUI 1235 and presenting, on the display, the video conference in the video conference 1240.

Automatic Inventory Management

Another example of the surgical suite optimization engine performing an action to optimize the ophthalmic surgery suite involves determining when an inventory level is low and automatically ordering new inventory. In some surgical procedures, consumable accessories are used to ensure sterility. Consumable accessories can include a tag (e.g. RFID tag) or other means to identify the consumable accessory in order for the surgical console to determine that the right surgical accessory is being used for the procedure and for the particular patient. Also, the tag can be used to manage inventory of consumable accessories, e.g. in an inventory management system. In some embodiments of the present technology, the surgical suite optimization engine can determine when particular consumable accessories are used (e.g. when they are scanned when being connected with a surgical console) and can automatically re-order inventory when a level of the consumable accessory falls beneath a predetermined threshold level of inventory.

Figure 13:
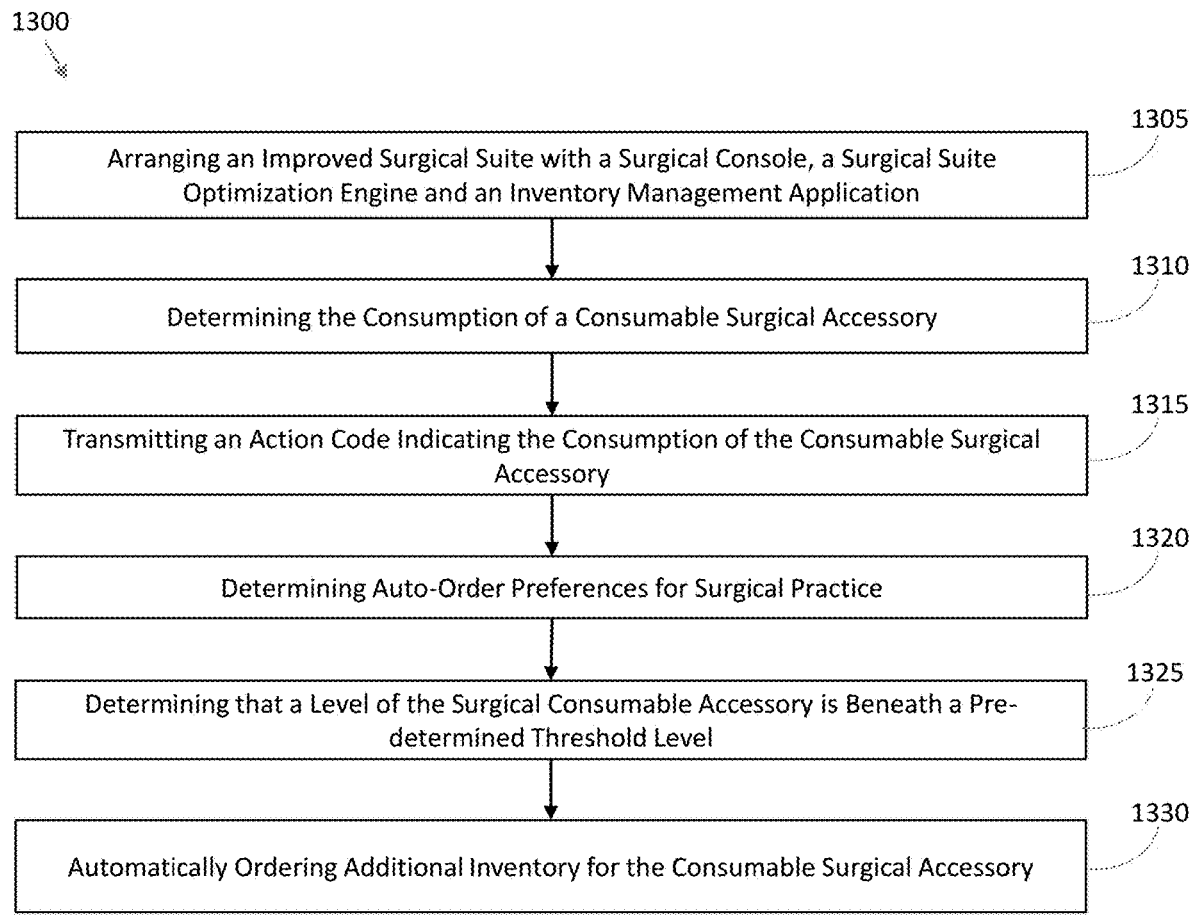
FIG. 13 illustrates a method of a surgical suite optimization engine maintaining appropriate inventory for a surgical practice.

FIG. 13 illustrates a method 1300 of a surgical suite optimization engine maintaining appropriate inventory for a surgical practice. The method 1300 involves arranging an improved surgical suite with a surgical console, a surgical suite optimization engine and an inventory management application 1305. Next, the method 1300 involves determining the consumption of a consumable surgical accessory 1310 (e.g. by a surgical console reading an RFID tag of a consumable accessory), and transmitting an action code indicating the consumption of the consumable surgical accessory 1315.

Next, the method 1300 involves a surgical suite optimization engine determining auto-order preferences for surgical practice 1320 (e.g. by accessing preferences for a surgical practice stored in a database in the surgical suite optimization engine) and determining that a level of the surgical consumable accessory is beneath a pre-determined threshold level 1325, as defined in the auto-order preferences. Next, the method 1300 involves the surgical suite optimization engine automatically ordering additional inventory for the consumable surgical accessory 1330, as defined in the auto-order preferences.

Example System Architecture

Figure 14A:
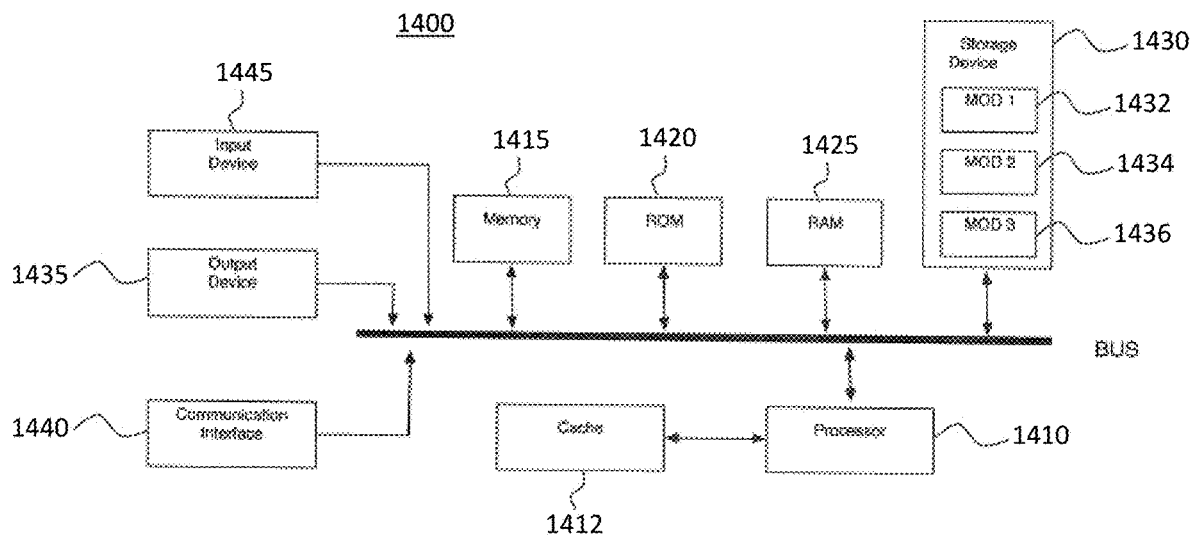
FIG. 14A and FIG. 14B illustrate exemplary possible system embodiments.
Figure 14B:
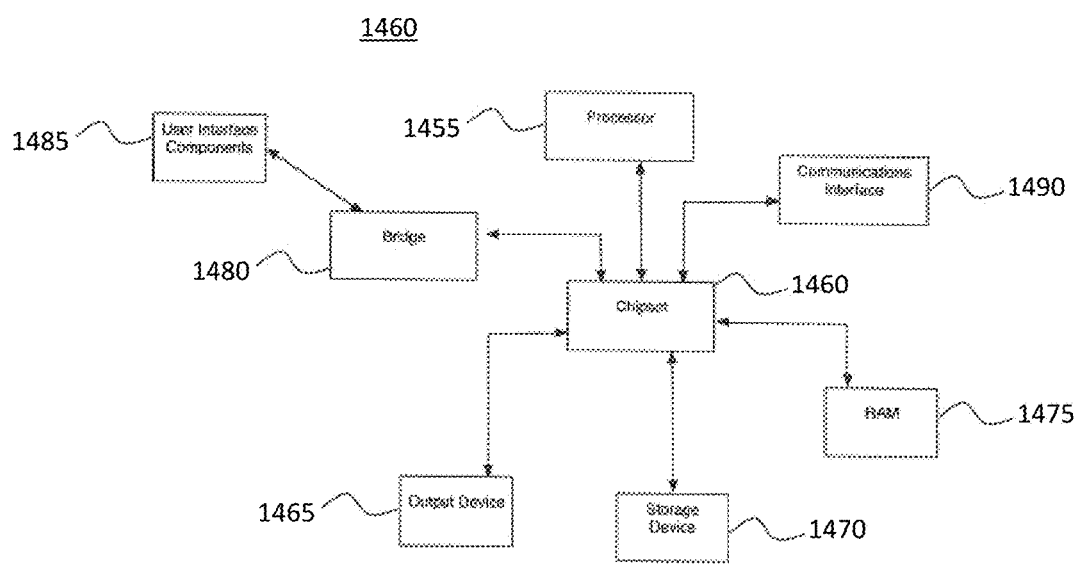

FIG. 14A and FIG. 14B illustrate possible system embodiments. The more appropriate embodiment will be apparent to those of ordinary skill in the art when practicing the present technology. Persons of ordinary skill in the art will also readily appreciate that other system embodiments are possible.

FIG. 14A illustrates a conventional system bus computing system architecture 1400 wherein the components of the system are in electrical communication with each other using a bus 1405. Exemplary system 1400 includes a processing unit (CPU or processor) 1410 and a system bus 1405 that couples various system components including the system memory 1415, such as read only memory (ROM) 1420 and random access memory (RAM) 1425, to the processor 1410. The system 1400 can include a cache of high-speed memory connected directly with, in close proximity to, or integrated as part of the processor 1410. The system 1400 can copy data from the memory 1415 and/or the storage device 1430 to the cache 1412 for quick access by the processor 1410. In this way, the cache can provide a performance boost that avoids processor 1410 delays while waiting for data. These and other modules can control or be configured to control the processor 1410 to perform various actions. Other system memory 1415 may be available for use as well. The memory 1415 can include multiple different types of memory with different performance characteristics. The processor 1410 can include any general purpose processor and a hardware module or software module, such as module 1 1432, module 2 1434, and module 3 1436 stored in storage device 1430, configured to control the processor 1410 as well as a special-purpose processor where software instructions are incorporated into the actual processor design. The processor 1410 may essentially be a completely self-contained computing system, containing multiple cores or processors, a bus, memory controller, cache, etc. A multi-core processor may be symmetric or asymmetric.

To enable user interaction with the computing device 1400, an input device 1445 can represent any number of input mechanisms, such as a microphone for speech, a touch-sensitive screen for gesture or graphical input, keyboard, mouse, motion input, speech and so forth. An output device 1435 can also be one or more of a number of output mechanisms known to those of skill in the art. In some instances, multimodal systems can enable a user to provide multiple types of input to communicate with the computing device 1400. The communications interface 1440 can generally govern and manage the user input and system output.

There is no restriction on operating on any particular hardware arrangement and therefore the basic features here may easily be substituted for improved hardware or firmware arrangements as they are developed.

Storage device 1430 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1425, read only memory (ROM) 1420, and hybrids thereof.

The storage device 1430 can include software modules 1432, 1434, 1436 for controlling the processor 1410. Other hardware or software modules are contemplated. The storage device 1430 can be connected to the system bus 1405. In one aspect, a hardware module that performs a particular function can include the software component stored in a computer-readable medium in connection with the necessary hardware components, such as the processor 1410, bus 1405, display 1435, and so forth, to carry out the function.

FIG. 14B illustrates a computer system 1450 having a chipset architecture that can be used in executing the described method and generating and displaying a graphical user interface (GUI). Computer system 1450 is an example of computer hardware, software, and firmware that can be used to implement the disclosed technology. System 1450 can include a processor 1455, representative of any number of physically and/or logically distinct resources capable of executing software, firmware, and hardware configured to perform identified computations. Processor 1455 can communicate with a chipset 1460 that can control input to and output from processor 855. In this example, chipset 860 outputs information to output 1465, such as a display, and can read and write information to storage device 1470, which can include magnetic media, and solid state media, for example. Chipset 1460 can also read data from and write data to RAM 1475. A bridge 1480 for interfacing with a variety of user interface components 1485 can be provided for interfacing with chipset 1460. Such user interface components 1485 can include a keyboard, a microphone, touch detection and processing circuitry, a pointing device, such as a mouse, and so on. In general, inputs to system 1450 can come from any of a variety of sources, machine generated and/or human generated.

Chipset 1460 can also interface with one or more communication interfaces 1490 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1455 analyzing data stored in storage 1470 or 1475. Further, the machine can receive inputs from a user via user interface components 1485 and execute appropriate functions, such as browsing functions by interpreting these inputs using processor 1455.

It can be appreciated that exemplary systems 1400 and 1450 can have more than one processor 1410 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An ophthalmic system comprising:
   a surgical console having tools for conducting an ophthalmic procedure, a console processor, and a console memory containing console instructions which, when executed by the console processor, cause the console processor to monitor a quantitative feature of the ophthalmic procedure and determine when to transmit an action code relating to the quantitative feature of the ophthalmic procedure; and
   a heads-up display communicatively coupled with the surgical console and a surgical camera for capturing a three-dimensional image of an eye, the heads-up display including a display screen for displaying the stereoscopic representation of the three-dimensional image of the eye, a network interface, and a surgical suite optimization engine (SSOE), wherein the SSOE includes an SSOE processor and an SSOE memory containing SSOE instructions which, when executed by the SSOE processor, cause the SSOE processor to perform an action after receiving the action code from the surgical console, wherein the action at least includes causing the heads-up display to launch an inventory management application that includes an input for a surgical staff member to enter, during a procedure, the consumption of a particular surgical supply and that tracks inventory of surgical supplies for a surgical practice in real time.

2. The ophthalmic system of claim 1, wherein the quantitative feature of the ophthalmic procedure comprises an operational status of a component of the surgical console, and wherein the console processor determines to issue an action code when the component malfunctions.

3. The ophthalmic system of claim 2, wherein the action performed by the SSOE comprises establishing, via the network interface, a video conference connection with a technical support center.

4. The ophthalmic system of claim 1, wherein the console instructions further cause the surgical console to access user preference data stored in the console memory, the user preference data describing user-defined adjustment in one or more of the plurality of procedure steps for a plurality of ophthalmic procedures.

5. The ophthalmic system of claim 1, wherein the console instructions further cause the surgical console to access procedure data stored in the console memory, the procedure data describing a plurality of procedure steps for a plurality of ophthalmic procedures.

6. The ophthalmic system of claim 5, wherein the quantitative feature of the ophthalmic procedure comprises a control limit for an aspect of one or more procedure step, and wherein the console processor determines to issue an action code when the aspect of the one or more procedure step comes within a predetermined proximity to the control limit.

7. The ophthalmic system of claim 6, wherein the action performed by the SSOE comprises displaying, on the display screen, an alert relating to the proximity to the control limit.

8. The ophthalmic system of claim 5, wherein the procedure data describes a plurality of surgical phases, wherein each surgical phase includes one or more procedure steps, and wherein the console processor determines to issue an action code at a transition between surgical phases.

9. The ophthalmic system of claim 8, wherein the heads-up display further includes an actuator for moving the heads-up display relative to a position of a surgeon operating on a patient eye, wherein the action performed by the SSOE comprises moving the heads-up display relative to the position of the surgeon at the transition between surgical phases.

10. The ophthalmic system of claim 9, wherein a first phase of surgery deals with a first region of the eye, wherein a second phase of surgery deals with a second region of the eye, and wherein the instruction to move the heads-up display relative to the position of the surgeon involves moving the heads-up display from a position to optimize a stereoscopic viewing distance of the first region of the eye to a position to optimize a stereoscopic viewing distance of the second region of the eye.

11. The ophthalmic system of claim 8, wherein the quantitative feature of the ophthalmic procedure comprises a transition point between a current procedure step and a subsequent procedure step, wherein the console processor determines to issue an action code when the transition point is detected.

12. The ophthalmic system of claim 11, wherein the action performed by the SSOE comprises the display processor automatically adjusting display parameters of the stereoscopic representation of the three-dimensional image of the eye.

13. The ophthalmic system of claim 12, wherein automatically adjusting display parameters further involves the display processor displaying one or more overlay over the stereoscopic representation of the three-dimensional image of the eye.

14. The ophthalmic system of claim 12, wherein automatically adjusting display parameters further involves the display processor filtering color attributes of the stereoscopic representation of the three-dimensional image to highlight one or more areas of the eye in the stereoscopic representation of the three-dimensional image.

15. The ophthalmic system of claim 12, wherein automatically adjusting display parameters further involves the display processor enhancing image features of the stereoscopic representation of the three-dimensional image.

16. The ophthalmic system of claim 11, further comprising:
a diagnostic imaging device for capturing a diagnostic image of the eye; and
a robotic arm configured to position and focus the diagnostic imaging device, wherein the console processor is configured to transmit a control signal to the robotic arm when the transition point is detected, wherein the control signal is interpreted by the robotic arm and causes the robotic arm to position and focus the diagnostic imaging device on an area of the eye that is a subject of the subsequent procedure step.

17. The ophthalmic system of claim 16, wherein the diagnostic imaging device is selected from among a group of diagnostic imaging devices consisting of an optical coherence tomography device, a reflectance interferometer, an ultrasonic device, and an extended depth of field device.

18. The ophthalmic system of claim 1, wherein the surgical console includes a laser treatment component configured to emit an aiming beam and a treatment beam.

19. The ophthalmic system of claim 18, wherein the aiming beam has a wavelength in in a range of 620 nanometers to 750 nanometers and the treatment beam has a wavelength in in a range of 495 nanometers to 570 nanometers.

20. The ophthalmic system of claim 19, wherein the quantitative feature of the ophthalmic procedure comprises an indication relating to whether the laser treatment component is emitting the aiming beam or the treatment beam, wherein the console processor determines to transmit an action code when the laser treatment transitions between an emission of the aiming beam and an emission of the treatment beam.

21. The ophthalmic system of claim 20, wherein the action comprises performing digital signal processing to maximize red contract of the stereoscopic representation of the three-dimensional image of the eye when the laser treatment transitions from the emission of the treatment beam to the emission of the aiming beam.

22. The ophthalmic system of claim 20, wherein the action performed by the SSOE comprises performing digital signal processing to neutralize a green flashback from a retina in the stereoscopic representation of the three-dimensional image of the eye when the laser treatment transitions from the emission of the aiming beam to the emission of the treatment beam.

23. The ophthalmic system of claim 1, further comprising:
a further component of a surgical suite, the further component communicatively coupled with the SSOE and configured to transmit communication having a form or syntax that is not recognized by the ophthalmic system; and a transcoding engine configured to receive communication from a first component of a surgical suite and transcode the communication into a form and syntax recognized by the ophthalmic system.

24. The ophthalmic system of claim 1, further comprising:
an eye tracking sensor configured to track a position of at least one anatomical structure of the eye; and
a robotic arm for moving the surgical camera, wherein the surgical camera is configured to receive the position of the at least one anatomical structure of the eye from the eye tracking sensor and control the robotic arm to move the surgical camera to remain centered on the eye.

25. The ophthalmic system of claim 1, further comprising stereoscopic glasses configured to filter light from the display screen.

26. The ophthalmic system of claim 25, wherein the stereoscopic glasses contain a motion tracker and a network interface, wherein the motion tracker tracks movement of the stereoscopic glasses, and wherein the network interface transmits a gaze signal to the heads-up display describing the movement of the stereoscopic glasses.

27. The ophthalmic system of claim 26, wherein the display instructions further cause the display processor to display a pointer on the display screen and move the pointer in response to the movement of the stereoscopic glasses.

28. The ophthalmic system of claim 27, wherein the display instructions further cause the display processor to:
determine that the movement of the stereoscopic glasses caused the pointer to move to an on-screen item displayed on the display screen; and
activate a function of the on-screen item when the pointer remains positioned on the on-screen item for a predetermined threshold time period.

29. The ophthalmic system of claim 28, wherein the on-screen item comprises a menu and the function comprises interacting with the menu using the pointer.

30. The ophthalmic system of claim 26, wherein the motion tracker comprises a plurality of accelerometers.

31. The ophthalmic system of claim 1, wherein display screen comprises a touchscreen interface, and wherein the display processor is configured to recognize touch gestures received via the touchscreen interface.

32. The ophthalmic system of claim 1, wherein the one or more applications includes an application for directly initiating a voice and/or video communication with a technical support representative.

33. The ophthalmic system of claim 1, wherein the one or more applications includes an application for directly initiating a voice and/or video communication with a customer service representative.

34. The ophthalmic system of claim 1, wherein the one or more applications includes an application for directly initiating a voice and/or video communication with a sales representative.

35. The ophthalmic system of claim 1, wherein the one or more applications includes an interactive surgical planning application.

36. The ophthalmic system of claim 1, wherein the one or more applications includes an application for receiving, via the network interface, and displaying preoperative diagnostic images for a patient.

37. The ophthalmic system of claim 1, wherein the display memory contains further instructions which, when executed by the display processor, cause the display processor to automatically order, via the network interface, a predetermined amount of the particular surgical supply.

* * * * *